(12) United States Patent
Lee et al.

(10) Patent No.: US 11,357,774 B2
(45) Date of Patent: Jun. 14, 2022

(54) USE OF A QUINOLINE SULFONYL COMPOUND FOR TREATMENT OF INFLAMMATION, INFLAMMATORY DISORDERS, AUTOIMMUNE DISORDERS AND MALARIA

(71) Applicants: Hoyun Lee, Cookstown (CA); Amanda Durkin, Sudbury (CA)

(72) Inventors: Hoyun Lee, Cookstown (CA); Amanda Durkin, Sudbury (CA)

( * ) Notice: Subject to any disclaimer, the term of this patent is extended or adjusted under 35 U.S.C. 154(b) by 0 days.

(21) Appl. No.: 16/808,916

(22) Filed: Mar. 4, 2020

(65) Prior Publication Data

US 2020/0281920 A1 Sep. 10, 2020

Related U.S. Application Data

(60) Provisional application No. 62/814,330, filed on Mar. 6, 2019.

(51) Int. Cl.
  *A61K 31/496* (2006.01)
  *A61P 29/00* (2006.01)
  *A61P 33/06* (2006.01)

(52) U.S. Cl.
  CPC ............ *A61K 31/496* (2013.01); *A61P 29/00* (2018.01); *A61P 33/06* (2018.01)

(58) Field of Classification Search
  CPC ......... A61K 31/496; A61P 29/00; A61P 33/06
  See application file for complete search history.

(56) References Cited

U.S. PATENT DOCUMENTS

2012/0269797 A1* 10/2012 Schubert .................. A61P 37/00
  424/130.1

FOREIGN PATENT DOCUMENTS

WO WO2014134705 A1 9/2014

OTHER PUBLICATIONS

Pundir, S., et al., VR23: A Quinoline-Sulfonyl Hybrid Proteasome Inhibitor That Selectively Kills Cancer via Cyclin E-Mediated Centrosome Amplification. Cancer Res, 2015. 75(19): p. 4164-75.
Statistics Canada, Table 13-10-0394-01: Leading causes of death, total population, by age group. 2016.
Shah, A., Fitzgerald D, and Murray F, Non-steroidal anti-inflammatory drugs (NSAIDs) and gastro-intestinal toxicity: Current issues. Irish Journal of Medical Science, 1999. 168(4): p. 242-245.
Bhala, N., et al., Vascular and upper gastrointestinal effects of non-steroidal anti-inflammatory drugs: meta-analyses of individual participant data from randomised trials. Lancet, 2013. 382: p. 769-779.

Barnes, P.J., Anti-inflammatory actions of glucocorticoids: molecular mechanisms. Clinical Science, 1998. 94(6): p. 557-572.
Moghadam—Kia, S. and Werth V.P., Prevention and treatment of systemic glucocorticoid side effects. International Journal of Dermatology, 2010. 49(3): p. 239-248.
Aulakh, R. and Singh S., Strategies for minimizing corticosteroid toxicity: a review. Indian Journal of Pediatrics, 2008. 75(10): p. 1067-1073.
National Institutes of Health, The Autoimmune Diseases Coordinating Committee, Progress in Autoimmune Disease Research, in Report to Congress. 2005, National Institute of Allergy and Infectious Diseases, National Institutes of Health: Bethesda, MD.
Verbrugge, S.E., et al., Proteasome inhibitors as experimental therapeutics of autoimmune diseases. Arthritis Research & Therapy, 2015. 17(1): p. 17.
Forlenza, O.V., et al., Increased serum IL-1beta level in Alzheimer's disease and mild cognitive impairment. Dement Geriatr Cogn Disord, 2009. 28, p. 507-12.
Whiteley, W., et al., Inflammatory markers and poor outcome after stroke: a prospective cohort study and systematic review of interleukin-6. PLoS Med, 2009. 6(9): e1000145.
Cesari, M., et al., Inflammatory markers and onset of cardiovascular events: results from the Health ABC study. Circulation, 2003. 108(19): p. 2317-22.
Li, H., Manwani B., and Leng S. X., Frailty, inflammation, and immunity. Aging Dis, 2011. 2(6): p. 466-73.
Giovannini, S., et al., Interleukin-6, C-reactive protein, and tumor necrosis factor-alpha as predictors of mortality in frail, community-living elderly individuals. J Am Geriatr Soc, 2011. 59(9): p. 1679-85.
Puchta, A., et al., TNF Drives Monocyte Dysfunction with Age and Results in Impaired Anti-pneumococcal Immunity. PLoS Pathogens, 2016. 12(1): e1005368.
Paats, M.S., et al., Local and systemic cytokine profiles in nonsevere and severe community-acquired pneumonia. Eur Respir J, 2013. 41(6): p. 1378-85.
Yende, S., et al., Inflammatory markers at hospital discharge predict subsequent mortality after pneumonia and sepsis. Am J Respir Crit Care Med, 2008, 177, p. 1242-7.
De Flora, S. and La Maestra, S., Epidemiology of cancers of infectious origin and prevention strategies. J Prev Med Hyg, 2015, 56(1): p. E15-20.
Van Tong, H., et al., Parasite Infection, Carcinogenesis and Human Malignancy. EBioMedicine, 2017, 15: p. 12-23.
Vichai, V. and Kirtikara, K. Sulforhodamine B colorimetric assay for cytotoxicity screening. Nature Protocols, 2006, 1(3): p. 1112-1116.
Hu, C., et al., The efficacy and selectivity of tumor cell killing by Akt inhibitors are substantially increased by chloroquine. Bioorganic & Medicinal Chemistry, 2008, 16, p. 7888-7893.
Skehan, P., et al., New colorimetric cytotoxicity assay for anticancer-drug screening. J Natl Cancer Inst, 1990, 82(13): p. 1107-12.

(Continued)

*Primary Examiner* — Sarah Pihonak
(74) *Attorney, Agent, or Firm* — Bereskin & Parr LLP/S.E.N.C.R.L., s.r.l.

(57) ABSTRACT

The present application relates to uses of 7-chloro-4-(4-(2, 4-dinitrophenylsulfonyl)piperazin-1-yl)quinoline (VR23) or optionally a pharmaceutically acceptable salt, solvate or prodrug thereof, for the treatment of malaria or for treatment of a disease, disorder or condition treatable by reducing or inhibiting the secretion of a pro-inflammatory cytokine and/or reducing myeloperoxidase such as inflammation, an inflammatory disorder or autoimmune disease.

4 Claims, 20 Drawing Sheets

(56) References Cited

OTHER PUBLICATIONS

Justus, C.R., et al., In vitro cell migration and invasion assays. Journal of Visualized Experiments, 2014. 88: e51046.

Crandall, I.E., et al., Antimalarial activities of 6-iodouridine and its prodrugs and potential for combination therapy. J Med Chem, 2013. 56(6): p. 2348-58.

Wei, D. and Huang Z., Anti-inflammatory effects of triptolide in LPS-induced acute lung injury in mice. Inflammation, 2014. 37(4): p. 1307-1316.

Jeong, J.Y. and Jue D.M., Chloroquine inhibits processing of tumor necrosis factor in lipopolysaccharide-stimulated RAW 264.7 macrophages. The Journal of Immunology, 1997. 158(10): p. 4901-4907.

Karres, I., et al., Chloroquine inhibits proinflammatory cytokine release into human whole blood. American Journal of Physiology-Regulatory, Integrative and Comparative Physiology, 1998. 274(4): p. R1058-R1064.

Picot, S., et al., Chloroquine inhibits tumor necrosis factor production by human macrophages in vitro. J Infect Dis, 1991. 164(4): p. 830.

Zhu, X., et al., Chloroquine inhibits macrophage tumour necrosis factor-alpha mRNA transcription. Immunology, 1993. 80(1): p. 122-126.

Chang, J.-H., et al., Validity of SW982 synovial cell line for studying the drugs against rheumatoid arthritis in fluvastatin-induced apoptosis signaling model. Indian Journal of Medical Research, 2014. 139(1): p. 117.

Yoshida, Y. and Tanaka T., Interleukin 6 and rheumatoid arthritis. BioMed Research International, 2014. 698313.

Clark, P., et al., Hydroxychloroquine Compared with Placebo in Rheumatoid Arthritis: A Randomized Controlled Trial. Ann Intern Med, 1993. 119(11): p. 1067-1071.

Molad, Y., et al., Protective effect of hydroxychloroquine in systemic lupus erythematosus. Prospective long-term study of an Israeli cohort. Lupus, 2002. 11(6): p. 356-361.

Ben-Zvi, I., et al., Hydroxychloroquine: from malaria to autoimmunity. Clinical Reviews in Allergy & Immunology, 2012. 42(2): p. 145-153.

Grommes, J. and Soehnlein O., Contribution of neutrophils to acute lung injury. Molecular Medicine, 2011. 17(3-4): p. 293-307.

Pulli, B., et al., Measuring myeloperoxidase activity in biological samples. PloS One, 2013. 8(7): p. e67976.

Gabay, C., Interleukin-6 and chronic inflammation. Arthritis Research & Therapy, 2006. 8(2): p. S3.

Noss, E.H. and Brenner M.B., The role and therapeutic implications of fibroblast—like synoviocytes in inflammation and cartilage erosion in rheumatoid arthritis. Immunological reviews, 2008. 223(1): p. 252-270.

Ni, Y.-F., et al., Histone deacetylase inhibitor, butyrate, attenuates lipopolysaccharide-induced acute lung injury in mice. Respiratory Research, 2010. 11(1): p. 33.

Wang, D., et al., Peptidoglycans promotes human leukemic THP-1 cell apoptosis and differentiation. Asian Pacific Journal of Cancer Prevention, 2012. 13(12): p. 6409-6413.

Kraus, J., et al., The novel 32-selective proteasome inhibitor LU-102 decreases phosphorylation of I kappa B and induces highly synergistic cytotoxicity in combination with ibrutinib in multiple myeloma cells. Cancer Chemotherapy and Pharmacology, 2015. 76(2): p. 383-396.

Jia, L., et al., Blocking autophagy prevents bortezomib-induced NF-κB activation by reducing I-κBα degradation in lymphoma cells. PloS One, 2012. 7(2): p. e32584.

Ali, A., et al., Novel N-arylpyrazolo [3, 2-c]-based ligands for the glucocorticoid receptor: receptor binding and in vivo activity. Journal of Medicinal Chemistry, 2004. 47(10): p. 2441-2452.

Heslop, C.L., Frohlich J.J., and Hill J.S., Myeloperoxidase and C-reactive protein have combined utility for long-term prediction of cardiovascular mortality after coronary angiography. J Am Coll Cardiol, 2010. 55(11): p. 1102-9.

* cited by examiner

USE OF A QUINOLINE SULFONYL COMPOUND FOR TREATMENT OF INFLAMMATION, INFLAMMATORY DISORDERS, AUTOIMMUNE DISORDERS AND MALARIA

CROSS-REFERENCE TO RELATED APPLICATIONS

The present application claims the benefit of priority from U.S. Patent Application No. 62/841,330 filed Mar. 6, 2019, the contents of which are incorporated by reference in their entirety.

FIELD

The present application relates to uses of 7-chloro-4-(4-(2,4-dinitrophenylsulfonyl)piperazin-1-yl)quinoline (VR23, a quinoline sulfonyl compound) or optionally a pharmaceutically acceptable salt, solvate or prodrug thereof, for the treatment of malaria or a disease, disorder or condition treatable by reducing or inhibiting the secretion of a pro-inflammatory cytokine and/or reducing myeloperoxidase such as inflammation, an inflammatory disorder and/or autoimmune disease.

BACKGROUND 7-chloro-4-(4-(2,4-dinitrophenylsulfonyl)piperazin-1-yl) quinolone (VR23), is a quinoline-sulfonyl hybrid compound[1]. VR23 is a strong proteasome inhibitor targeting the β2 subunit of the proteasome 20S catalytic unit[2]. Data from in vitro studies showed that VR23 preferentially kills cancer over non-cancer cells. Animal-based studies revealed that VR23 has strong anti-tumor activity without any notable toxic side effects to mouse organs[2]. Furthermore, VR23 also reduces toxic side effects caused by paclitaxel (Tax) when used in combination[2].

The inflammatory response is an important part of the immune system that works to prevent and eliminate foreign invaders such as viruses and bacteria. However, it may cause harmful health effects to hosts if not properly regulated. For example, overcompensation of the inflammatory response may lead to general inflammatory conditions such as acute lung injury (ALI), as well as serious diseases like autoimmune disorders.

General inflammatory conditions are still a significant issue, as they cause numerous deaths and disabilities worldwide. In Canada, chronic lower respiratory disease including bronchitis, emphysema and asthma is currently the fifth most common cause of death, causing approximately 12,000 deaths per year[3]. These conditions are largely linked to the dysregulation of the inflammatory response. Current drugs frequently used to treat general inflammatory conditions are non-steroidal anti-inflammatory drugs (NSAIDs)[4]. Although generally effective, these drugs often cause serious gastrointestinal complications such as ulceration, hemorrhage, and even death[4]. The use of NSAIDs is also correlated to an increased risk for vascular and coronary problems and heart failure[5]. In addition to NSAIDs, glucocorticoids are often used to treat chronic inflammatory conditions. These are a class of corticosteroids, which work by up-regulating anti-inflammatory proteins and down-regulating multiple inflammatory genes[6]. Dexamethasone (DEX), one of these corticosteroids, is effective at reducing inflammation. However, its prolonged use can lead to serious side effects on the musculoskeletal function, endocrine regulation, and cardiovascular and central nervous systems[7,8].

Autoimmune diseases such as rheumatoid arthritis are often caused by a high level of pro-inflammatory cytokines. Autoimmune disorders have been estimated to affect 50 million people in the U.S alone, with the prevalence still on the rise[9]. Current treatments for autoimmune diseases include methotrexate, glucocorticoids, and biological agents[10]. However, the long-term use of anti-rheumatics as the primary treatment has not been very successful as patients often develop resistance to these drugs.

Due to the low efficacy of current anti-rheumatic drugs and the toxic side effects of common anti-inflammatory drugs, alternative agents to combat inflammatory conditions that are more efficient and/or safer are therefore desirable.

Increases in serum cytokines (especially IL6 and TNF) are often correlated with the risk of aging-related diseases, including dementia[11], stroke[12], cardiovascular diseases[13], frailty[4,15], and certain microbial infections such as infections by S. pneumonia[16]. Although a robust inflammatory response is thought to be protective against infection, high levels of circulating inflammatory cytokines during pneumonia are associated with more severe disease and high mortality[7,18].

Malaria is a life-threatening disease caused mainly by Plasmodium parasites that are transmitted to people through the bites of infected female Anopheles mosquitoes. According to World Health Organization (WHO), there are 216 million cases of malarial infections world-wide and 445,000 deaths by this disease per year. Plasmodium falciparum, the deadliest species of Plasmodium, may also contribute to the development of lymphoma. This may occur through the toll-like receptors (TLR7 and TLR10)-mediated proliferation of plasma cells, thereby increasing the secretion of IgM and cytokines[19,20]. Early diagnosis and treatment of malaria can reduce the severity of the disease and prevent deaths. However, resistance to anti-malarial medicines is a recurring problem. Resistance of P. falciparum to medicines including HCQ, sulfadoxine-pyrimethamine (SP), and more recently artemisinin (Art) is a significant problem. Accordingly, alternative anti-malarial agents that may be useful to solve this problem are therefore desirable.

SUMMARY

It has been found that VR23 possesses anti-inflammatory, anti-rheumatoid arthritis, and anti-malarial activities. For example, in the studies described in greater detail hereinbelow, VR23 was found to have useful anti-malarial agent activity over chloroquine (CQ) and was more potent than HCQ, a well-known anti-inflammatory and anti-rheumatoid arthritis agent in cell studies.

Accordingly, the present application includes a method of treating a disease, disorder or condition treatable by reducing or inhibiting the secretion of a pro-inflammatory cytokine and/or reducing myeloperoxidase levels, the method comprising administering a therapeutically effective amount of 7-chloro-4-(4-(2,4-dinitrophenylsulfonyl)piperazin-1-yl) quinoline or a pharmaceutically acceptable salt, solvate or prodrug thereof to a subject in need thereof. The present application also includes a use of a therapeutically effective amount of 7-chloro-4-(4-(2,4-dinitrophenylsulfonyl)piperazin-1-yl)quinoline or a pharmaceutically acceptable salt, solvate or prodrug thereof for treating a disease, disorder or condition treatable by reducing or inhibiting the secretion of a pro-inflammatory cytokine and/or reducing myeloperoxidase levels in a subject; a use of 7-chloro-4-(4-(2,4-dinitrophenylsulfonyl)piperazin-1-yl)quinoline or a pharmaceutically acceptable salt, solvate or prodrug thereof for preparation of a medicament for treating a disease, disorder or condition treatable by reducing or inhibiting the secretion of a pro-inflammatory cytokine and/or reducing myeloperoxidase levels in a subject; and 7-chloro-4-(4-(2,4-dinitrophenylsulfonyl)piperazin-1-yl)quinoline or a pharmaceutically acceptable salt, solvate or prodrug thereof for use to treat a disease, disorder or condition treatable by reducing or inhibiting the secretion of a pro-inflammatory cytokine and/or reducing myeloperoxidase levels in a subject.

The present application also includes a method of treating malaria, the method comprising administering a therapeutically effective amount of 7-chloro-4-(4-(2,4-dinitrophenylsulfonyl)piperazin-1-yl)quinoline or a pharmaceutically acceptable salt, solvate or prodrug thereof to a subject in need thereof. The present application also includes a use of a therapeutically effective amount of 7-chloro-4-(4-(2,4-dinitrophenylsulfonyl)piperazin-1-yl)quinoline or a pharmaceutically acceptable salt, solvate or prodrug thereof for treating malaria in a subject; a use of 7-chloro-4-(4-(2,4-dinitrophenylsulfonyl)piperazin-1-yl)quinoline or a pharmaceutically acceptable salt, solvate or prodrug thereof for preparation of a medicament for treating malaria in a subject; and 7-chloro-4-(4-(2,4-dinitrophenylsulfonyl)piperazin-1-yl)quinoline or a pharmaceutically acceptable salt, solvate or prodrug thereof for use to treat malaria in a subject.

In an embodiment, 7-chloro-4-(4-(2,4-dinitrophenylsulfonyl)piperazin-1-yl)quinoline is administered to the subject or for use to treat the subject, as the case may be. In other words, the compound of the application that is administered or for use is not in the form of a pharmaceutically acceptable salt, solvate or prodrug.

In another embodiment, the subject is a human.

Other features and advantages of the present application will become apparent from the following detailed description. It should be understood, however, that the detailed description and the specific examples while indicating embodiments of the application are given by way of illustration only, since various changes and modifications within the spirit and scope of the application will become apparent to those skilled in the art from this detailed description.

BRIEF DESCRIPTION OF THE DRAWINGS

The present application will now be described in greater detail with reference to the drawings, in which.

DETAILED DESCRIPTION

I. Definitions

Figure 1:
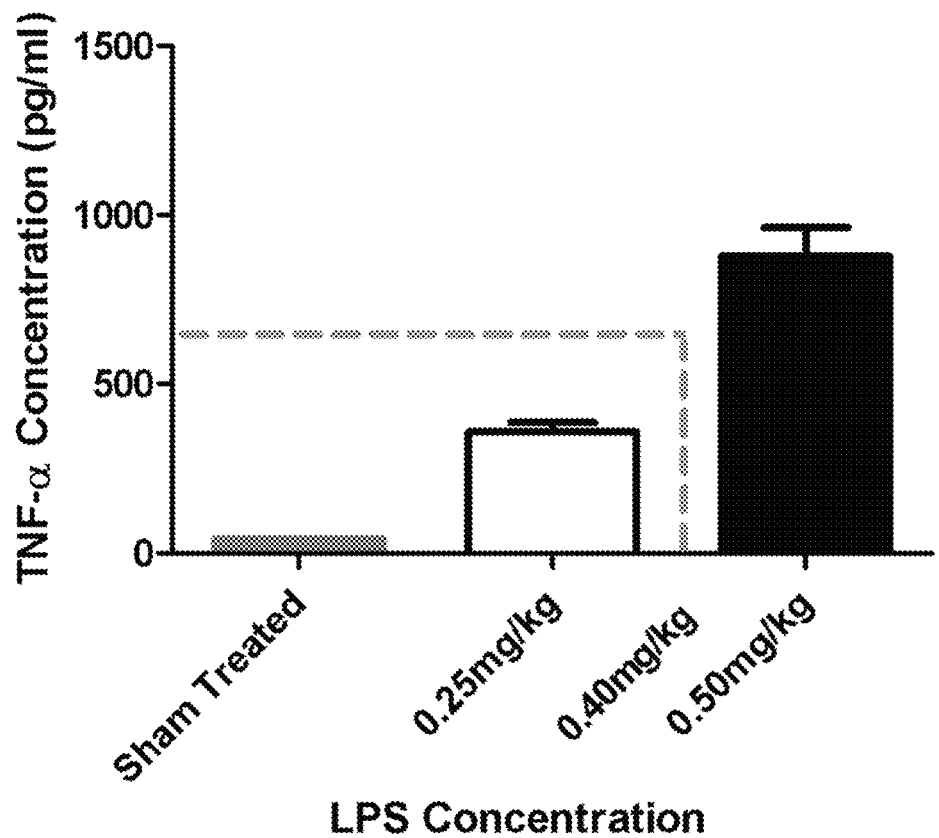
FIG. 1 is a plot of TNF-α concentration (pg/mL) in bronchoalveolar lavage fluid of mice treated intranasally with LPS concentrations of 0.25, 0.40 and 0.50 mg/kg as well as a sham control for 24 hours for the determination of a useful LPS concentration for the induction of TNF-α in the mouse lung. The values presented are the mean±SEM (n=3 for each group).

Unless otherwise indicated, the definitions and embodiments described in this and other sections are intended to be applicable to all embodiments and aspects of the present application herein described for which they are suitable as would be understood by a person skilled in the art.

In understanding the scope of the present application, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps.

Terms of degree such as "substantially", "about" and "approximately" as used herein mean a reasonable amount of deviation of the modified term such that the end result is not significantly changed. These terms of degree should be construed as including a deviation of at least ±5% of the modified term if this deviation would not negate the meaning of the word it modifies.

The term "and/or" as used herein means that the listed items are present, or used, individually or in combination. In effect, this term means that "at least one of" or "one or more" of the listed items is used or present.

As used in this application, the singular forms "a", "an" and "the" include plural references unless the content clearly dictates otherwise.

The term "VR23" as used herein refers to the compound 7-chloro-4-(4-(2,4-dinitrophenylsulfonyl)piperazin-1-yl)quinoline, having the chemical structure:

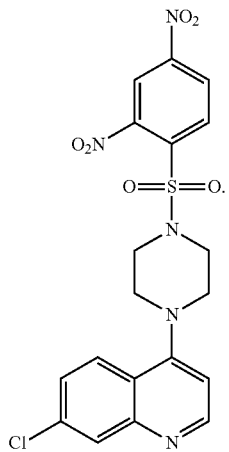

The term "subject" as used herein includes all members of the animal kingdom including mammals, and optionally refers to humans.

The term "compounds of the application" and the like as used herein refers to VR23 or a pharmaceutically acceptable salt, solvate or prodrug thereof.

The term "pharmaceutically acceptable" means compatible with the treatment of subjects, for example, mammals such as humans.

The term "pharmaceutically acceptable salt" as used herein means an acid addition salt that is compatible with the treatment of subjects.

An "acid addition salt that is compatible with the treatment of subjects" is any non-toxic organic or inorganic salt of any basic compound. Basic compounds that form an acid addition salt include, for example, compounds comprising an amine group susceptible to protonation. Illustrative inorganic acids which form suitable salts include hydrochloric, hydrobromic, sulfuric and phosphoric acids, as well as metal salts such as sodium monohydrogen orthophosphate and potassium hydrogen sulfate. Illustrative organic acids that form suitable salts include mono-, di-, and tricarboxylic acids such as glycolic, lactic, pyruvic, malonic, succinic, glutaric, fumaric, malic, tartaric, citric, ascorbic, maleic, benzoic, phenylacetic, cinnamic and salicylic acids, as well as sulfonic acids such as p-toluene sulfonic and methane-sulfonic acids. Such salts may exist in a hydrated, solvated or substantially anhydrous form. In general, acid addition salts are more soluble in water and various hydrophilic organic solvents, and generally demonstrate higher melting points in comparison to their free base forms. The selection of a suitable salt can be made by a person skilled in the art. The formation of a desired acid addition salt is, for example, achieved using standard techniques. For example, the neutral compound is treated with the desired acid in a suitable solvent and the salt which is thereby formed then isolated by filtration, extraction and/or any other suitable method.

The term "solvates" as used herein in reference to a compound refers to complexes formed between the compound and a solvent from which the compound is precipitated or in which the compound is made. Accordingly, the term "solvate" as used herein means a compound, or a salt of a compound, wherein molecules of a suitable solvent are incorporated in the crystal lattice. Examples of suitable solvents are ethanol, water and the like. When water is the solvent, the molecule is optionally referred to as a "hydrate". The formation of solvates will vary depending on the compound and the solvate. In general, solvates are formed by dissolving the compound in an appropriate solvent and isolating the solvate by cooling or using an antisolvent. The solvate is typically dried or azeotroped under ambient conditions. The selection of suitable conditions to form a particular solvate can be made by a person skilled in the art.

The term "prodrug" as used herein in reference to a compound refers to a derivative of the compound that reacts under biological conditions to provide the compound. In an embodiment, the prodrug comprises a conventional ester formed with an available amino group. For example, an available amino group is acylated using an activated acid in the presence of a base, and optionally, in an inert solvent (e.g. an acid chloride in pyridine). Some common esters which have been used as prodrugs are phenyl esters, aliphatic (C1-C24) esters, acyloxymethyl esters, carbamates and amino acid esters.

The compounds of the application are, for example, administered to the subject or used in an "effective amount".

As used herein, the term "effective amount" and the like means an amount effective, at dosages and for periods of time necessary to achieve a desired result. For example, in the context of treating malaria, an effective amount of the compounds of the application is an amount that, for example, reduces the malaria compared to the malaria without administration of the compounds of the application. Effective amounts may vary according to factors such as the disease state, age, sex, weight and/or species of the subject. The amount of a given compound that will correspond to such an amount will vary depending upon various factors, such as the given compound, the pharmaceutical formulation, the route of administration, the type of condition, disease or disorder being treated, the identity of the subject being treated, and the like, but can nevertheless be routinely determined by one skilled in the art.

II. Methods of Treatment and Uses

Unlike other proteasome inhibitors such as bortezomib (BTZ) and carfilzomib (CFZ), VR23 was found to reduce or inhibit the secretion of a wide range of pro-inflammatory cytokines including IL-1=β8, TNF-α, IL-6 and IL-8, indicating that VR23 may be useful to treat inflammation and inflammatory-related disorders. VR23 was also found to down-regulate the secretion of IL-6 in human synoviocytes isolated from rheumatoid arthritis patients and to down-regulate IL-6 and TNF-α in human peripheral blood mononuclear cells (PBMCs), indicating that VR23 may be useful for the treatment of autoimmune diseases including rheumatoid arthritis, systemic lupus erythematosus, psoriasis, inflammatory bowel diseases, and other similar autoimmune diseases. VR23 was also found to inhibit the migration of synovial cells, indicating that it may be useful to inhibit further deterioration of rheumatoid arthritis. It was also found that alveolar inflammation caused by LPS in a mouse model is largely prevented when the animals were treated with VR23, therefore VR23 may be useful to treat ALI and related diseases. VR23 was also found to reduce the levels of myeloperoxidase (MPO) in the bronchoalveolar space of the ALI mouse model therefore VR23 may be useful for reducing cardiovascular diseases and related mortality as an elevated level of MPO is a risk factor for cardiovascular-related mortality. Since VR23 reduces the levels of TNF-α and IL-6, it may be useful for treatment of aging-related diseases including dementia, stroke, frailty and microbial infections, for example *S. pneumonia* infections.

Accordingly, the present application includes a method of treating a disease, disorder or condition treatable by reducing or inhibiting the secretion of a pro-inflammatory cytokine and/or reducing myeloperoxidase levels, the method comprising administering a therapeutically effective amount of 7-chloro-4-(4-(2,4-dinitrophenylsulfonyl)piperazin-1-yl)quinoline or a pharmaceutically acceptable salt, solvate or prodrug thereof to a subject in need thereof. The present application also includes a use of a therapeutically effective amount of 7-chloro-4-(4-(2,4-dinitrophenylsulfonyl)piperazin-1-yl)quinoline or a pharmaceutically acceptable salt, solvate or prodrug thereof for treating a disease, disorder or condition treatable by reducing or inhibiting the secretion of a pro-inflammatory cytokine and/or reducing myeloperoxidase levels in a subject; a use of 7-chloro-4-(4-(2,4-dinitrophenylsulfonyl)piperazin-1-yl)quinoline or a pharmaceutically acceptable salt, solvate or prodrug thereof for preparation of a medicament for treating a disease, disorder or condition treatable by reducing or inhibiting the secretion of a pro-inflammatory cytokine and/or reducing myeloperoxidase levels in a subject; and 7-chloro-4-(4-(2,4-dinitrophenylsulfonyl)piperazin-1-yl)quinoline or a pharmaceutically acceptable salt, solvate or prodrug thereof for use to treat a disease, disorder or condition treatable by reducing or inhibiting the secretion of a pro-inflammatory cytokine and/or reducing myeloperoxidase levels in a subject.

In an embodiment, the method is for treating a disease, disorder or condition treatable by reducing or inhibiting the secretion of a pro-inflammatory cytokine. In another embodiment, the use is to treat a disease, disorder or condition treatable by reducing or inhibiting the secretion of a pro-inflammatory cytokine.

In an embodiment, the method is for treating a disease, disorder or condition treatable by reducing myeloperoxidase levels. In another embodiment of the present application, the use is to treat a disease, disorder or condition treatable by reducing myeloperoxidase levels.

In an embodiment, 7-chloro-4-(4-(2,4-dinitrophenylsulfonyl)piperazin-1-yl)quinoline is administered to the subject or for use to treat the subject, as the case may be. In other words, the compound of the application that is administered or for use is not in the form of a pharmaceutically acceptable salt, solvate or prodrug.

In an embodiment, the pro-inflammatory cytokine is selected from IL-1β, TNF-α, IL-6, IL-8 and combinations thereof. In another embodiment, the pro-inflammatory cytokine is IL-1β. In a further embodiment, the pro-inflammatory cytokine is TNF-α. In another embodiment of the present application, the pro-inflammatory cytokine is IL-6. In a further embodiment, the pro-inflammatory cytokine is IL-8. In another embodiment, the pro-inflammatory cytokine is a combination of two or more of IL-1β, TNF-α, IL-6 and IL-8.

In an embodiment, the disease, disorder or condition is selected from inflammation, an inflammatory disorder, an autoimmune disease, an allergic disease, a cardiovascular disease and an age-related disease.

In an embodiment, the disease, disorder or condition is inflammation. In another embodiment, the inflammation is selected from acute lung injury, bronchitis, emphysema and asthma.

In an embodiment, the disease, disorder or condition is an inflammatory disorder or autoimmune disorder. In another embodiment, the inflammatory disorder or autoimmune disease is selected from rheumatoid arthritis, systemic lupus erythematosus, psoriasis, inflammatory bowel disease and Crohn's disease. In a further embodiment, the disease, disorder or condition is rheumatoid arthritis. In another embodiment, the disease, disorder or condition is systemic lupus erythematosus. In a further embodiment, the disease, disorder or condition is psoriasis. In another embodiment of the present application, the disease, disorder or condition is inflammatory bowel disease. In a further embodiment, the disease, disorder or condition is Crohn's disease.

In an embodiment, the disease, disorder or condition is an allergic disease.

In an embodiment, the disease, disorder or condition is a cardiovascular disease.

In an embodiment, the disease, disorder or condition is an age-related disease. In another embodiment, the age-related disease is selected from dementia, stroke, frailty and microbial infection. In a further embodiment, the microbial infection is a *Streptococcus pneumonia* infection.

In an embodiment, the subject is human.

The present application also includes a method of reducing or inhibiting the secretion of a pro-inflammatory cytokine and/or reducing myeloperoxidase levels, in a cell, either in a biological sample or in a subject, the method comprising administering an effective amount of 7-chloro-4-(4-(2,4-dinitrophenylsulfonyl)piperazin-1-yl)quinoline or a pharmaceutically acceptable salt, solvate or prodrug thereof to the cell. The present application also includes a use of an effective amount of 7-chloro-4-(4-(2,4-dinitrophenylsulfonyl)piperazin-1-yl)quinoline or a pharmaceutically acceptable salt, solvate or prodrug thereof for reducing or inhibiting the secretion of a pro-inflammatory cytokine and/or reducing myeloperoxidase levels in a cell; a use of 7-chloro-4-(4-(2,4-dinitrophenylsulfonyl)piperazin-1-yl)quinoline or a pharmaceutically acceptable salt, solvate or prodrug thereof for preparation of a medicament for reducing or inhibiting the secretion of a pro-inflammatory cytokine and/or reducing myeloperoxidase levels in a cell; and 7-chloro-4-(4-(2,4-dinitrophenylsulfonyl)piperazin-1-yl) quinoline or a pharmaceutically acceptable salt, solvate or prodrug thereof for use to reduce or inhibit the secretion of a pro-inflammatory cytokine and/or reducing myeloperoxidase levels in a cell.

In an embodiment, the method is for reducing or inhibiting the secretion of a pro-inflammatory cytokine. In another embodiment, the use is to reduce or inhibit the secretion of a pro-inflammatory cytokine.

In an embodiment, the method is for reducing myeloperoxidase levels. In another embodiment, the use is to reduce myeloperoxidase levels.

In an embodiment, 7-chloro-4-(4-(2,4-dinitrophenylsulfonyl)piperazin-1-yl)quinoline is administered to the cell or for use to treat the cell, as the case may be. In other words, the compound of the application that is administered or for use is not in the form of a pharmaceutically acceptable salt, solvate or prodrug.

In an embodiment, the pro-inflammatory cytokine is selected from IL-1β, TNF-α, IL-6, IL-8 and combinations thereof. In another embodiment, the pro-inflammatory cytokine is IL-1β. In a further embodiment, the pro-inflammatory cytokine is TNF-α. In another embodiment of the present application, the pro-inflammatory cytokine is IL-6. In a further embodiment, the pro-inflammatory cytokine is IL-8. In another embodiment, the pro-inflammatory cytokine is a combination of two or more of IL-1β, TNF-α, IL-6 and IL-8.

In an embodiment, the cell is in a biological sample. In an embodiment, the cell is in a subject. In another embodiment, the subject is human.

VR23 was also found to possess anti-malarial activity and is surprisingly more effective on the CQ-resistant ItG strain than the CQ-sensitive 3D7 strain. Accordingly, VR23 may be useful as an anti-malarial agent.

Accordingly, the present application also includes a method of treating malaria, the method comprising administering a therapeutically effective amount of 7-chloro-4-(4-(2,4-dinitrophenylsulfonyl)piperazin-1-yl)quinoline or a pharmaceutically acceptable salt, solvate or prodrug thereof to a subject in need thereof. The present application also includes a use of a therapeutically effective amount of 7-chloro-4-(4-(2,4-dinitrophenylsulfonyl)piperazin-1-yl)quinoline or a pharmaceutically acceptable salt, solvate or prodrug thereof for treating malaria in a subject; a use of 7-chloro-4-(4-(2,4-dinitrophenylsulfonyl)piperazin-1-yl)quinoline or a pharmaceutically acceptable salt, solvate or prodrug thereof for preparation of a medicament for treating malaria in a subject; and 7-chloro-4-(4-(2,4-dinitrophenylsulfonyl)piperazin-1-yl)quinoline or a pharmaceutically acceptable salt, solvate or prodrug thereof for use to treat malaria in a subject.

In an embodiment, 7-chloro-4-(4-(2,4-dinitrophenylsulfonyl)piperazin-1-yl)quinoline is administered to the subject or for use to treat the subject, as the case may be. In other words, the compound of the application that is administered or for use is not in the form of a pharmaceutically acceptable salt, solvate or prodrug.

In an embodiment, the malaria is caused by *Plasmodium falciparum*. In another embodiment, the *Plasmodium falciparum* is a chloroquine (CQ)-resistant strain. In a further embodiment, the CQ-resistant strain is the ItG strain.

In an embodiment, the subject is a human.

Treatment methods or uses comprise administering to a subject or use of an effective amount of one or more compounds of the application, optionally consisting of a single administration or use, or alternatively comprising a series of administrations or uses. For example, the compounds of the application are administered or used at least once a week. However, in another embodiment, the one or more compounds of the application are administered to the subject or used from one time per three weeks, or one time per week to once daily for a given treatment or use. In another embodiment, the compounds are administered or used 2, 3, 4, 5 or 6 times daily. The length of the treatment period or use depends on a variety of factors, such as the severity of the disease, disorder, condition (or malaria), as the case may be, the age of the subject, the concentration of the one or more compounds of the application in a formulation, and/or a combination thereof. It will also be appreciated that the therapeutically effective amount of a compound used for the treatment or use in some embodiments may optionally increase or decrease over the course of a particular treatment regime or use. Changes in dosage may result and become apparent by standard diagnostic assays known in the art. In some instances, chronic administration or use is required. For example, the one or more compounds of the present application are administered or used in an amount and for a duration sufficient to treat the subject.

The compounds of the application can be administered to a subject or used in a variety of forms depending on the selected route of administration or use, as will be understood by those skilled in the art. In an embodiment, the one or more compounds of the disclosure are administered to the subject, or used, by oral (including buccal) or parenteral (including intravenous, intraperitoneal, subcutaneous, intramuscular, transepithelial, nasal, intrapulmonary, intrathecal, rectal, topical, patch, pump and transdermal) administration or use and the compound(s) formulated accordingly. For example, the compounds of the disclosure are administered or used in an injection, in a spray, in a tablet/caplet, in a powder, topically, in a gel, in drops, by a patch, by an implant, by a slow release pump or by any other suitable method of administration or use, the selection of which can be made by a person skilled in the art.

In an embodiment, the one or more compounds of the present disclosure are orally administered or used, for example, with an inert diluent or with an assimilable edible carrier, or enclosed in hard or soft shell gelatin capsules, or compressed into tablets, or incorporated directly with the food of the diet. In an embodiment, for oral administration or use, the one or more compounds of the disclosure are incorporated with excipient and administered or used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained-release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as molecular sieving type particles, or, a fine hollow permeable fiber bundle, or chopped hollow permeable fibers, agglomerated or held in a fibrous packet. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. In an embodiment, liposomes are formed from a variety of phospholipids, such as cholesterol, stearylamine and/or phosphatidylcholines.

In another embodiment, the compounds of the application are administered or used parenterally. Solutions of the compounds of the application are, for example, prepared in water optionally mixed with a surfactant such as hydroxypropylcellulose. In a further example, dispersions are prepared in glycerol, liquid polyethylene glycols, DMSO and mixtures thereof with or without alcohol, and in oils. Pharmaceutical forms suitable for injectable administration or use include sterile aqueous solutions or dispersions and sterile powders for the extemporaneous preparation of sterile injectable solutions or dispersions. A person skilled in the art would know how to prepare suitable formulations.

The compounds of the application including pharmaceutically acceptable salts, solvates and prodrugs thereof are suitably used on their own but will generally be administered or used in the form of a pharmaceutical composition in which one or more compounds of the application (the active ingredient) is in association with a pharmaceutically acceptable carrier. Depending on the mode of administration or use, the pharmaceutical composition will comprise from about 0.05 wt % to about 99 wt % or about 0.10 wt % to about 70 wt %, of the active ingredient (one or more compounds of the application), and from about 1 wt % to about 99.95 wt % or about 30 wt % to about 99.90 wt % of a pharmaceutically acceptable carrier, all percentages by weight being based on the total composition.

Compounds of the application may be used alone or in combination with other known agents useful for treating malaria or treating diseases, disorders or conditions treatable by reducing or inhibiting the secretion of a pro-inflammatory cytokine and/or reducing myeloperoxidase levels. When used in combination with other such agents, it is an embodiment that the compounds of the application are administered or used contemporaneously with those agents. As used herein, "contemporaneous administration" or "contemporaneous use" of two substances to a subject means providing each of the two substances so that they are both biologically active in the individual at the same time. The exact details of the administration or use will depend on the pharmacokinetics of the two substances in the presence of each other, and can include administering or use of the two substances within a few hours of each other, or even administering or use of one substance within 24 hours of administration or use of the other, if the pharmacokinetics are suitable. Design of suitable dosing regimens is routine for one skilled in the art. In particular embodiments, two substances will be administered or used substantially simultaneously, i.e., within minutes of each other, or in a single composition that contains both substances. It is a further embodiment of the present application that a combination of agents is administered to a subject or used in a non-contemporaneous fashion. In an embodiment, a compound of the application is administered or used with another agent simultaneously or sequentially in separate unit dosage forms or together in a single unit dosage form. Accordingly, the present application provides a single unit dosage form comprising one or more compounds of the application, an additional agent, and a pharmaceutically acceptable carrier.

The dosage of compounds of the application can vary depending on many factors such as the pharmacodynamic properties of the compound, the mode of administration or use, the age, health and weight of the recipient, the nature and extent of the symptoms, the frequency of the treatment, the type of concurrent treatment, if any, and the clearance rate of the compound in the subject to be treated. One of skill in the art can determine the appropriate dosage based on the above factors. Compounds of the application may be administered or used initially in a suitable dosage that in some embodiments may optionally be adjusted as required, depending on the clinical response. Dosages will generally be selected to maintain a serum level of compounds of the application from about 0.01 µg/cc to about 1000 µg/cc, or about 0.1 µg/cc to about 100 µg/cc. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. For parenteral administration or use, a representative amount is from about 0.001 mg/kg to about 10 mg/kg, about 0.01 mg/kg to about 10 mg/kg, about 0.01 mg/kg to about 1 mg/kg or about 0.1 mg/kg to about 1 mg/kg will be administered. For oral administration or use, a representative amount is from about 0.001 mg/kg to about 10 mg/kg, about 0.1 mg/kg to about 10 mg/kg, about 0.01 mg/kg to about 1 mg/kg or about 0.1 mg/kg to about 1 mg/kg. Compounds of the application may be administered or used in a single daily, weekly or monthly dose or the total daily dose may be divided into two, three or four daily doses.

The following non-limiting examples are illustrative of the present application:

EXAMPLES

Example 1: Studies of the Effect of VR23 on Experimental Models Relating to Inflammation, Autoimmune Conditions, Malaria and Other Disorders I. Materials and Methods Reagents:

VR23 was synthesized by Dalton Pharma Services of Toronto, Ontario, Canada, following the general protocol described in WO 2014/134705 A1. VR23 stock solution (20 mM) was prepared in dimethyl sulfoxide (DMSO) as described previously[1,2]. Stock solutions for BTZ (1 mM) (Cedarlane, NC), CFZ (1 µM) (Cedarlane, NC), and DEX (1.5 mM) (Sigma Aldrich) were also similarly prepared in DMSO. HCQ (50 mM) (Sigma Aldrich) stock was prepared in deionized sterile water. The stock solutions (5 mg/mL) of LPS (Sigma Aldrich), TNF-α (1 µg/mL) (ThermoFisher) and IL-1β (50 µg/mL) (ThermoFisher) were prepared in deionized sterile water. Phytohaemagglutinin-P (PHA-p) (Sigma Aldrich) stock solution (1 mg/mL) was prepared with phosphate buffered saline. RPMI 1640, high glucose Dulbecco's Modified Eagle Medium (DMEM), FBS and antibiotic antimycotic solutions (penicillin/streptomycin) were purchased from ThermoFisher. The single-analyte enzyme linked immunosorbent assay (ELISA) kits were purchased from Qiagen. Cell Counting Kit-8 (CCK-8) was purchased from Enzo Life Sciences (Farmingdale, N.Y.).

Cell Lines and Cell Culture:

THP-1 monocytic cells were purchased from the American Type Culture Collection (ATCC); cultured in RPMI-1640 supplemented with 100 µg/mL streptomycin, 100 units/mL penicillin and 10% (v/v) FBS. The SW-982 synovial cell line, originally derived from a female patient with synovial sarcoma, was purchased from ATCC and cultured in the high glucose DMEM supplemented with 10% (v/v) FBS. Primary peripheral blood mononuclear cells were purchased from ATCC and cultured in AIM V serum free media purchased from ThermoFisher. All cells were incubated at 37° C. in an incubator under humidified conditions with 5% CO2 and 95% air. Human fibroblast-like synoviocytes (HFLS) isolated from rheumatoid arthritis patients (HFLS-RA) and non-rheumatic patients (HFLS-N) were purchased from Cell Applications (San Diego, Calif.) and cultured in the synoviocyte growth medium purchased from the supplier.

Determining $IC_{50}$ Values Using the Sulforhodamine B Colorimetric Assay:

The sulforhodamine B (SRB) assay[21] was used to determine the drug concentration that half of the cell growth/viability is inhibited ($IC_{50}$). Cells were cultured in 96-well plates, with 5,000 cells in 100 μL of culture medium per well. The rest of the protocol was the same as described previously[22,23].

Cell Counting Kit-8 Assay:

The CCK-8 assay was used to count viable cells under the various treatment conditions. Briefly, cells were cultured in 11 columns of a 96-well clustered plate, with 5,000 cells in 100 μL of culture medium per well, excluding one column for a media-only control. The plate was incubated overnight at 37° C. in the humidified conditions, followed by treatment with test compounds diluted in the culture medium (10 μL). Each column was treated with a different condition so that each treatment could have 8 repeats. The plate was incubated for 6 hours in the incubator under the normal cell culture conditions, followed by adding 10 μL of CCK-8 reagent to each well and incubation continued for two additional hours to allow colour formation. The absorbance was measured using an automatic plate reader (Synergy H4 Hybrid Multi-Mode Microplate Reader, BioTek, Montreal, Canada) at 450 nm wavelength. The cell viability of each treatment sample was determined by using the following equation (%)=(Abstrtmt-Absmedia)/(AbsuT-Absmedia)*100, where Abstrtmt is the absorbance value of cells with the various treatment conditions; Absmedia is the absorbance of the well containing media only; AbsuT is the absorbance of the wells with untreated cells.

Enzyme-Linked Immunosorbent Assay:

The enzyme-linked immunosorbent assay (ELISA) is a quantitative measurement based on sandwich-based enzyme linking, using a protein-specific capture antibody to determine the levels of single or multiple chemokines and cytokines. Single-Analyte ELISArray human kits (Qiagen) were used to detect/measure TNF-α, IL-1β, IL-6, and IL-8 cytokines, following the protocol suggested by the supplier. A mouse TNF-α ELISA Kit (ThermoFisher) was used for the analysis of the cytokine levels in the mouse bronchoalveolar lung fluid, as suggested by the supplier.

Cell Migration Assay:

Cell migration assays were performed with Corning invasion chambers with Matrigel matrix (Fisher Scientific). The lower chamber contained compounds (e.g., VR23 or HCQ) and FBS as a chemo-attractant. The upper chamber was loaded with cells in FBS-free medium. The analysis of the trans-well inserts were carried out as described previously[24]. After 24 hours of incubation, the trans-well inserts were removed, and then the remaining media and cells on the upper chamber were also removed from the top of the membrane with a cotton swab. The trans-well inserts were placed into wells containing 1 mL of 70% ethanol for 10 minutes to fix the cells. The residual ethanol was carefully removed with a cotton swab. Cells on the trans-well insert membrane were then air-dried at room temperature for 15 minutes. The trans-well insert containing cells were placed in 1 mL of 0.2% crystal violet for 10 minutes to stain. The excessive crystal violet was carefully removed from the membrane with a cotton swab. Subsequently, cells on the trans-well membrane were air-dried at room temperature prior to analysis under an inverted microscope. Images (10×) were captured at 5 different fields. The average number of cells that migrated through the membrane towards the chemo-attractant were determined. Adherent cells attach to the membrane on the lower chamber side upon migration and suspension cells drop into the lower chamber.

Anti-Malarial Study:

The CQ-resistant *P. falciparum* ItG and the CQ-sensitive 3D7 strains were maintained and assays carried out as described previously[25]. Briefly, *P. falciparum* strains were maintained in RPMI 1640 culture medium supplemented with 10% human serum, 25 mM HEPES, gentamicin, and 50 μM of hypoxanthine. The anti-parasitic assay was carried out as described previously[25]. Briefly, a compound gradient was generated across a 96-well assay plate; a constant number of parasites added in 50 μL of the culture medium; allowed to grow for 48 hours; and followed by the measurement of DNA amounts (i.e., fluorescence) using SYBR Green I. The $IC_{50}$ value is the 50% point between alive and dead for which a three-parameter fit was used.

Figure 2:
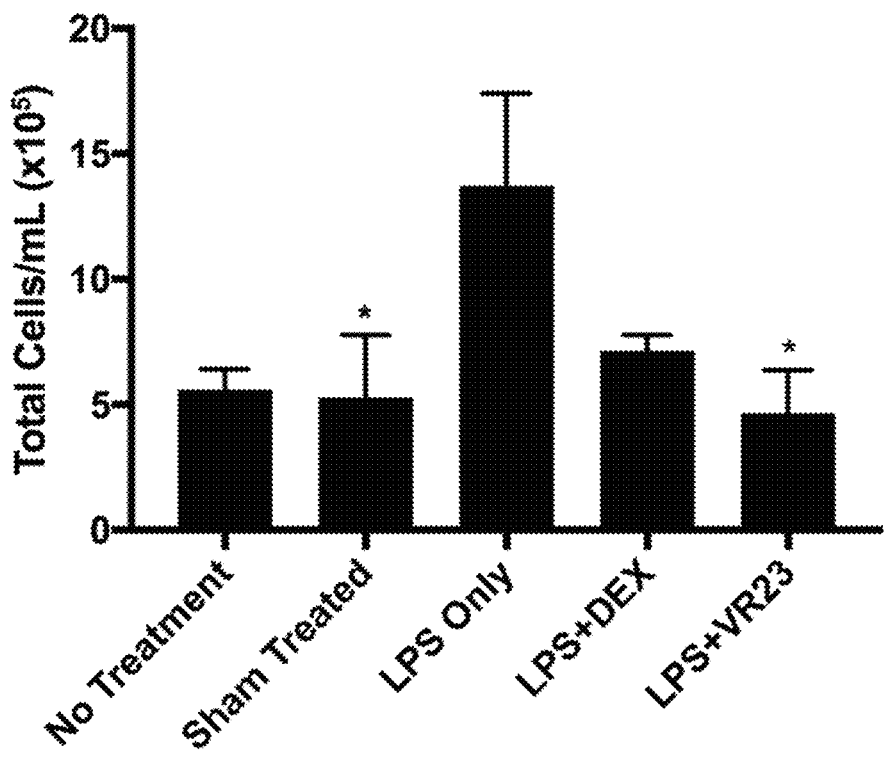
FIG. 2 is a plot showing the total cell counts per mL determined at 24-hour post-LPS stimulation of bronchoalveolar fluid of BALB/c mice with ALI caused by LPS treated with LPS+VR23 according to an embodiment of the present application in comparison to mice with no lung injury (i.e. no treatment), sham treated mice, mice treated with LPS-only and mice treated with LPS+DEX. * is p<0.05 and denotes a significant difference from the LPS-only group, determined by a Dunnett's test. The values presented are the mean±SEM (n=3-6 in each group).
Figure 3:
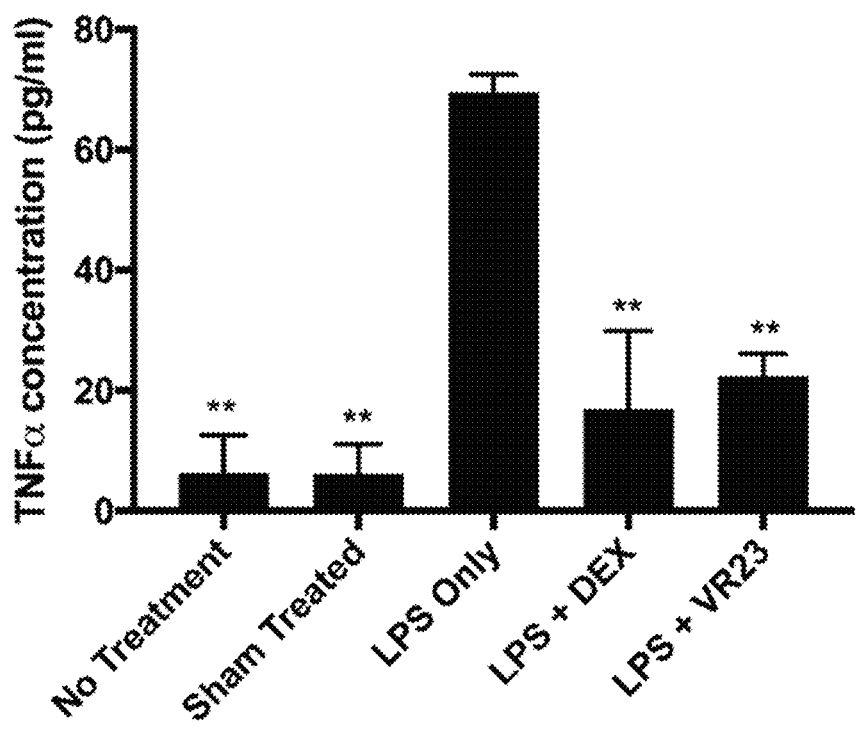
FIG. 3 is a plot showing the levels of the TNF-α inflammatory cytokine determined at 24-hours post-LPS stimulation in the bronchoalveolar fluid of mice with acute lung injury caused by LPS treated with LPS+VR23 according to an embodiment of the present application in comparison to mice with no lung injury (i.e. no treatment), sham treated mice, mice treated with LPS-only and mice treated with LPS+DEX. ** is p<0.01 and denotes a significant difference from the LPS-only group, determined by a Dunnett's test. The values presented are the mean±SEM (n=3-6 in each group).
Figure 4:
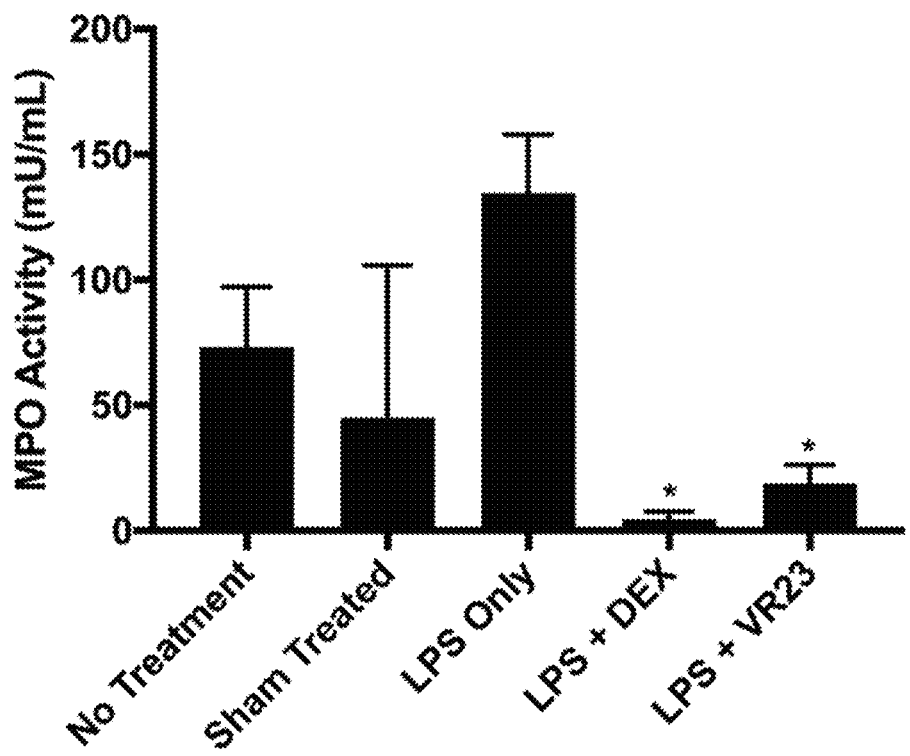
FIG. 4 shows the myeloperoxidase (MPO) activity in right lung tissues 24-hour post-LPS treatment of mouse lung tissues with acute injury caused by LPS (0.4 mg/kg) treated with LPS+VR23 according to an embodiment of the present application in comparison to mice with no lung injury (i.e. no treatment), sham treated mice, mice treated with LPS-only and mice treated with LPS+DEX. * is p<0.05 and denotes a significant difference from the LPS-only group, determined by a Dunnett's test. The values presented are the mean±SEM (n=3-6 in each group).
Figure 5:
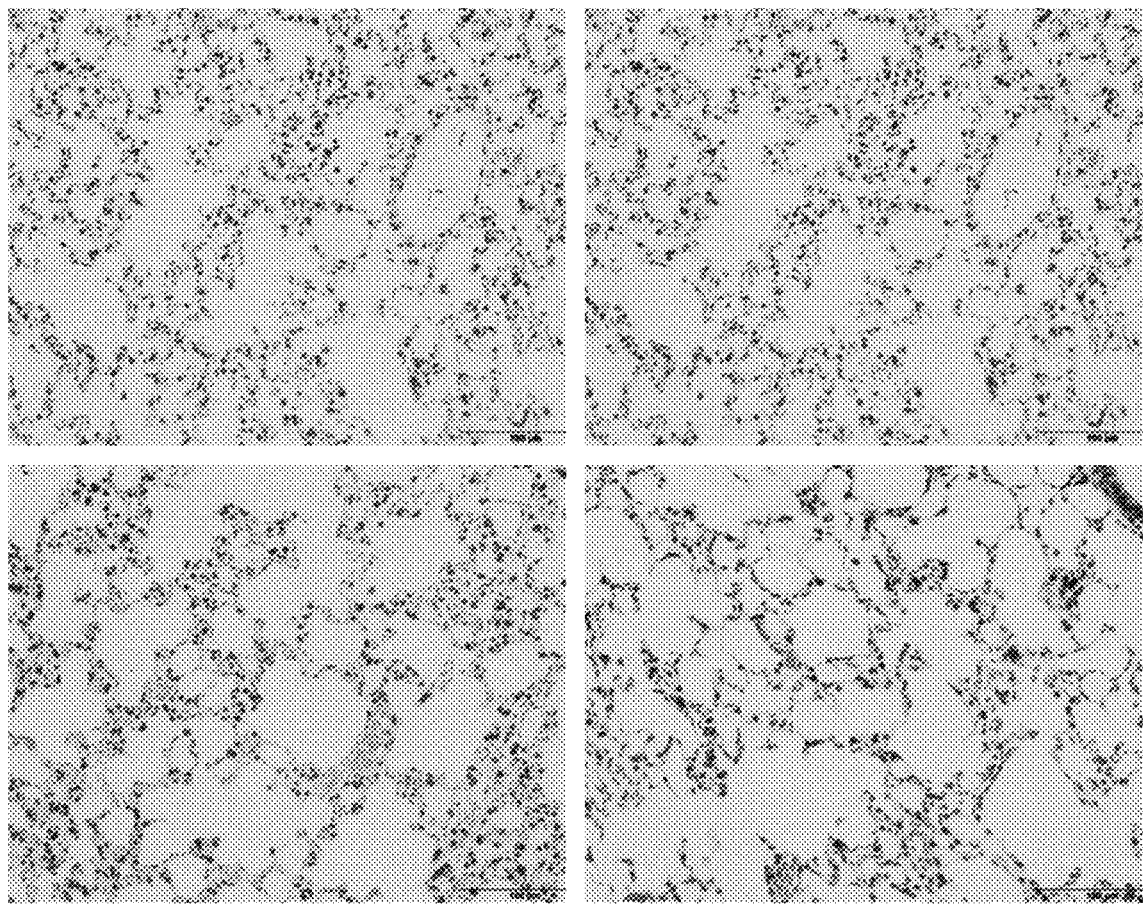
FIG. 5 shows exemplary micrographs showing histopathological changes in mouse lung tissues as a result of ALI caused by LPS (cf. untreated control: upper left image; mouse treated with LPS only: upper right image), which are largely inhibited by treatment of VR23 according to an embodiment of the present application (lower left image) or DEX (lower right image). Scale bars show 100 μm.

Animal Work:

Six to eight week old female BALB/c mice strain 028 (Charles River Laboratories, QC, Canada) were fed regularly with laboratory chow and water upon arrival at the Laurentian University Animal Care Facility (Sudbury, ON, Canada). To determine a useful dose of LPS, three mice per group were treated for 24 hours with the following three different conditions: (i) no LPS, (ii) 0.25 mg of LPS per kg of body weight, and (iii) 0.50 mg of LPS per kg of body weight. The different concentrations of LPS were administered intranasally to the three BALB/c mice per concentration. After the animals were sacrificed, the bronchoalveolar lavage fluid (BALF) of each mouse was collected and analyzed for LPS-induced inflammatory responses. FIG. 1 shows experimental data used to determine an optimal LPS concentration for the induction of TNF-α in the mouse lung. The results indicated that 0.40 mg/kg (i.e., between 0.25 mg/kg and 0.5 mg/kg) is a useful concentration. Experimental design involving the use of VR23 was based on a previous acute lung injury (ALI) instillation by Wei and Huang[26]. Briefly, mice were divided into 5 groups, with 3-5 mice per group: no lung injury (i.e., no treat), sham treated, LPS-only, LPS+DEX, and LPS+VR23. VR23 (30 mg/kg) and DEX (4 mg/kg) were intraperitoneally injected 1 hour prior to LPS administration. The mice were given LPS (0.4 mg/kg) in phosphate buffered saline (PBS) intranasally to induce ALI. The sham treated mice were given PBS intranasally plus DMSO-only (since VR23 was dissolved in DMSO) administered intraperitoneally. The mice were sacrificed by isoflurane inhalation at 24-hour post-induction of ALI with LPS. Bronchoalveolar lavage fluid was collected and the number of cells infiltrated into the bronchoalveolar fluid were counted (FIG. 2). The fluid was also used to determine the levels of TNF-α by ELISA (FIG. 3). The lungs were removed to determine the levels of myeloperoxidase (MPO) and histopathological analysis (FIG. 4 and FIG. 5, respectively). One unit of MPO activity is defined as the amount of enzyme that hydrolyzes the substrate to generate taurine chloramine to consume 1.0 μmole of 3,3',5,5'-Tetramethylbenzidine (TMB) per minute.

Myeloperoxidase Assay:

The accumulation of neutrophils in the lung tissues was analyzed with a colorimetric MPO assay kit (Sigma Aldrich), which measures the amount of myeloperoxidase activity[26]. At 24-hour post-induction of lung injury with LPS, the upper and lower lobes of the right lung were removed and snap frozen at −80° C. For analysis, the lungs were thawed, weighed, and homogenized with cold MPO assay buffer using a sonic dismembrator. The MPO activity was then determined as per the protocol provided by the supplier.

Histopathological Analysis:

At 24-hour post-induction of lung injury with LPS, lung tissues were embedded in the paraffin block, followed by slicing them into 10 μm sections using a microtome. Each slice was stained with H & E for the examination of cell morphology, chromosomes, mitotic cells, cells and tissue types, and other assays. For microscopy, at least 10 fields were analyzed for each sample.

Statistical Analyses:

Except where otherwise noted, each experiment was repeated three times. The mean values of these results were used for statistical analysis and are expressed as mean±standard error. Comparison between experimental groups was made by p value determination using one-way ANOVA. A p value of <0.05 was considered to be statistically significant. The Dunnett's post-hoc test was performed when necessary to determine the significance between the treatment groups and the control. Analyses were performed with GraphPad Prism software (GraphPad Software, Inc).

II. Results

Data shown in Table 1 are $IC_{50}$ values of VR23 and other compounds, which were determined using sulforhodamine B (SRB) assays on immunologically relevant cells (THP-1, SW-982 and PBMC). VR23 is much more potent than HCQ, a well-known anti-inflammatory and anti-rheumatoid arthritis agent[27]. Two well-known proteasome inhibitors, BTZ and CFZ, were included for comparison since VR23 is also a proteasome inhibitor, albeit targeting different subunits[2]. The widely used anti-inflammatory DEX was included, also for comparison.

TABLE 1

$IC_{50}$ values of VR23 in comparison to other compounds on THP-1, SW-982, and PBMC cells.

| $IC_{50}$ | VR23 (µM) | HCQ (µM) | BTZ (nM) | CFZ (nM) | DEX (µM) |
|---|---|---|---|---|---|
| SW982 | 4.33 ± 0.7 | 28.19 + 4.3 | — | — | — |
| THP-1 | 2.58 ± 0.5 | — | 5.91 ± 0.34 | 1.01 ± 0.11 | 2.067 ± 0.067 |
| PBMC | 3.14 ± 0.26 | — | 5.86 ± 0.3 | — | — |

THP-1, SW982 and PBMC cells (5,000 cells/well) were treated with each compound for 48 hours. The $IC_{50}$, the drug concentration reducing cell growth/viability by 50%, was determined by a dose-response four-parameter curve (generated with GraphPad Prism V. 4.02) formed by 10 two-fold dilutions (n=3).

Figure 6:
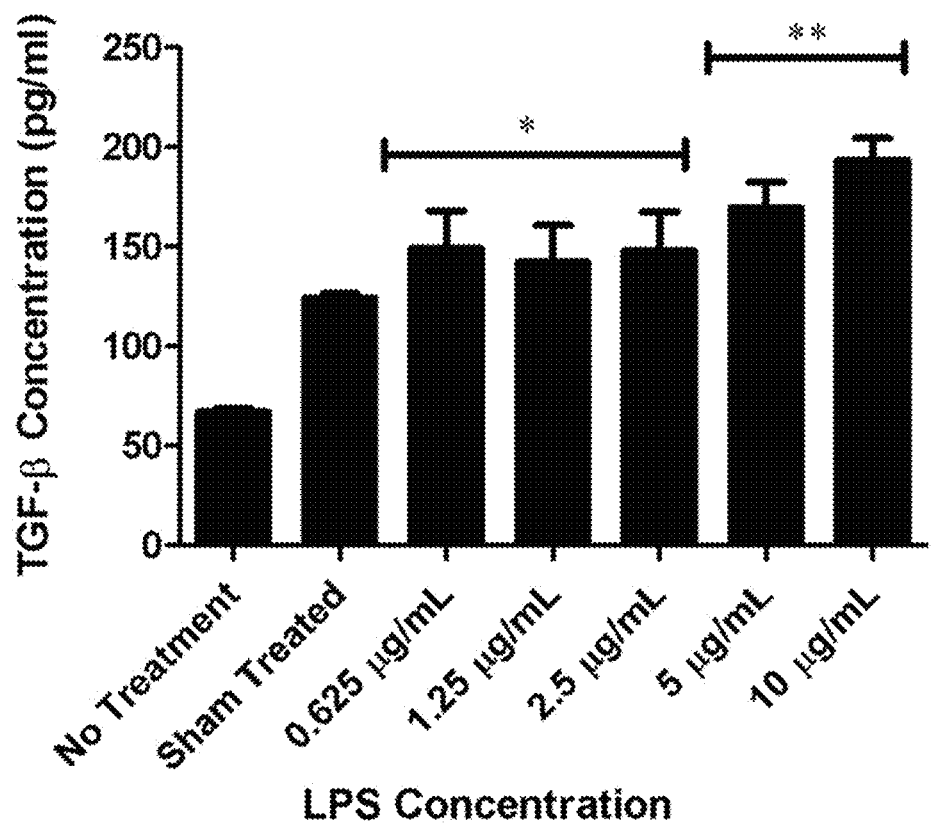
FIG. 6 shows data from an experiment carried out with THP-1 cells to determine a useful dose of LPS for the induction of TGF-β wherein THP-1 cells ($0.5 \times 10^6$/mL) were stimulated with varying doses (0, 0.625, 1.25, 2.5, 5 or 10 μg/mL) of E. coli LPS for 24 hours or received no treatment. The comparison between different groups was made by p value using Dunnett's test. * and ** are p<0.05 and p<0.01, respectively, which denote a significant difference from the non-treatment group. The values presented are the mean±SEM (n=3).
Figure 7:
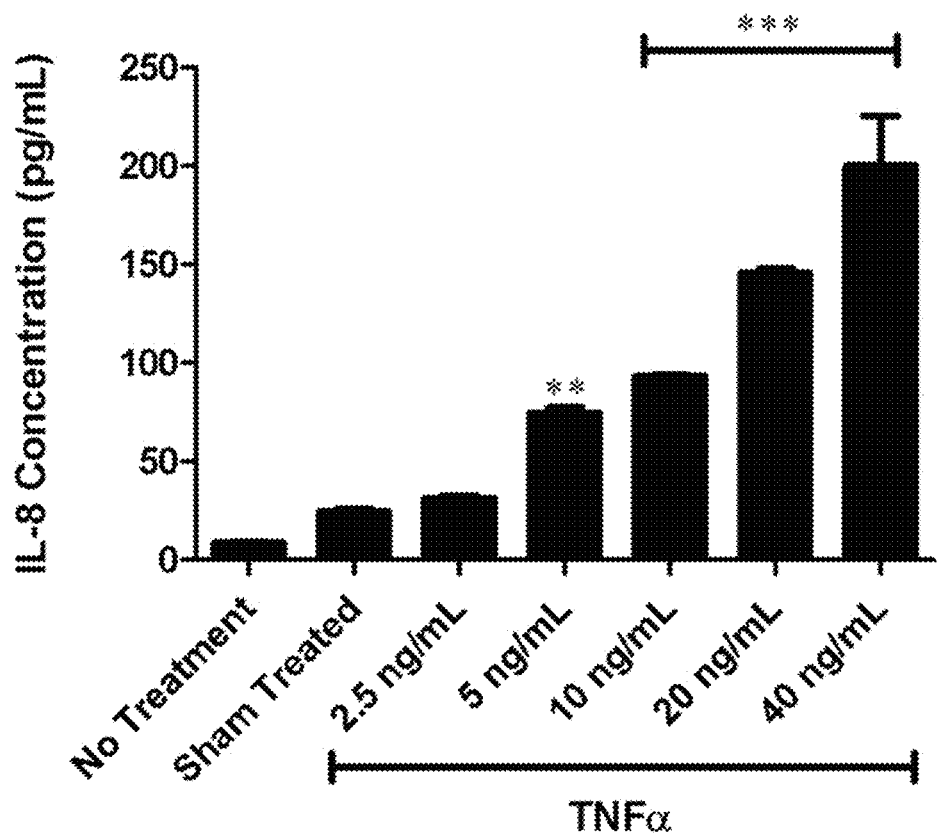
FIG. 7 shows data from an experiment carried out with THP-1 cells to determine a useful dose of TNFα for the induction of IL-8 wherein THP-1 cells ($0.5 \times 10^6$/mL) were stimulated with varying concentrations of TNF-α (0, 2.5, 5, 10, 20 or 40 ng/mL) for 24 hours or received no treatment. The comparison between different groups was made by p value using Dunnett's test.  and * are p<0.01 and p<0.001, respectively, which denote a significant difference from the non-treatment control group. The values presented are the mean±SEM (n=3).

The results of experiments carried out to determine useful concentrations of LPS and TNF-α for the induction of cytokines are shown in FIG. 6 and FIG. 7. FIG. 6 shows the levels of TGF-β secreted from THP-1 cells stimulated with varying concentrations of LPS. The cytokine secretion was measured in cell culture supernatants by a single-analyte ELISA. FIG. 7 shows the levels of IL-8 in THP-1 cells stimulated with varying concentrations of TNF-α. The amounts of cytokine secreted in cell culture supernatants were measured with a single-analyte ELISA. Data from the ELISA assays indicate that useful doses of LPS and TNF-α are 5 µg/mL and 10 ng/mL, respectively to stimulate THP-1 cells.

Figure 8:
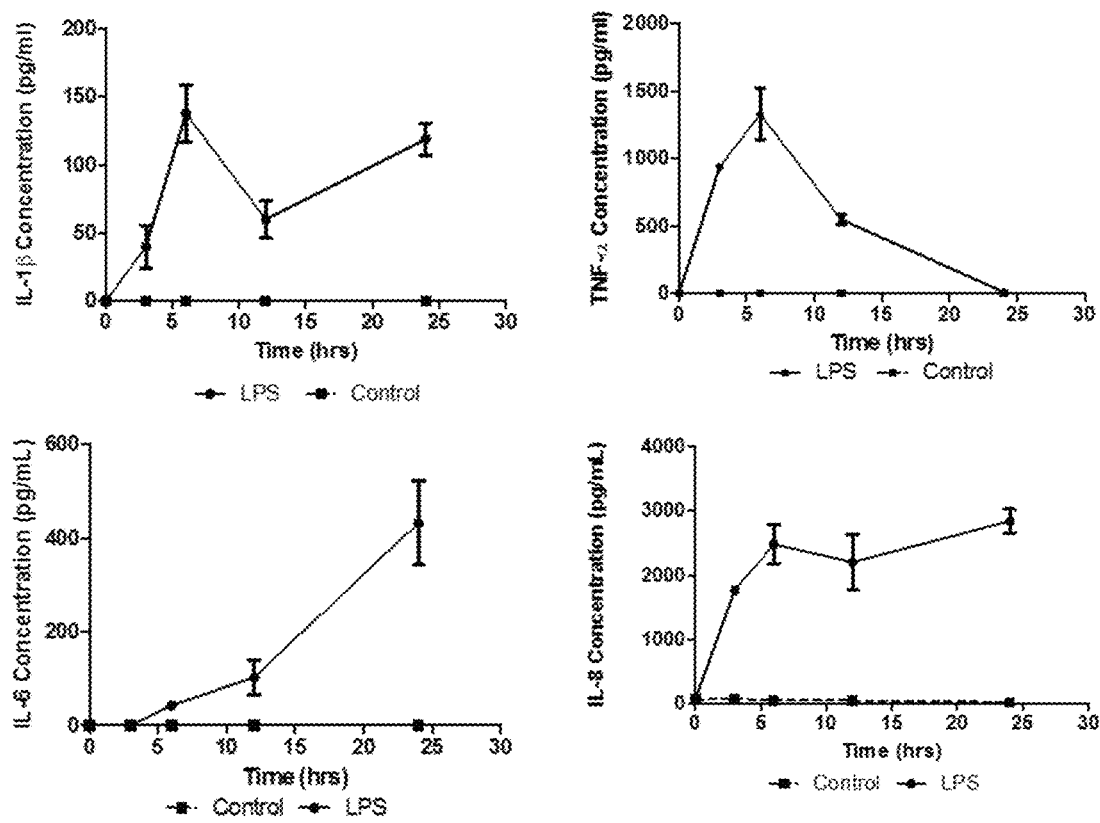
FIG. 8 shows plots of the levels of cytokine secretion as a function of time after THP-1 cells ($0.5 \times 10^6$/mL) were stimulated with 5 μg/mL of LPS wherein cytokines IL-1β (upper left plot), TNF-α (upper right plot), IL-6 (lower left plot), and IL-8 (lower right plot) in cell culture supernatants were measured at the indicated time points by a single-analyte ELISA. The values presented are the mean±SEM (n=3).
Figure 9:
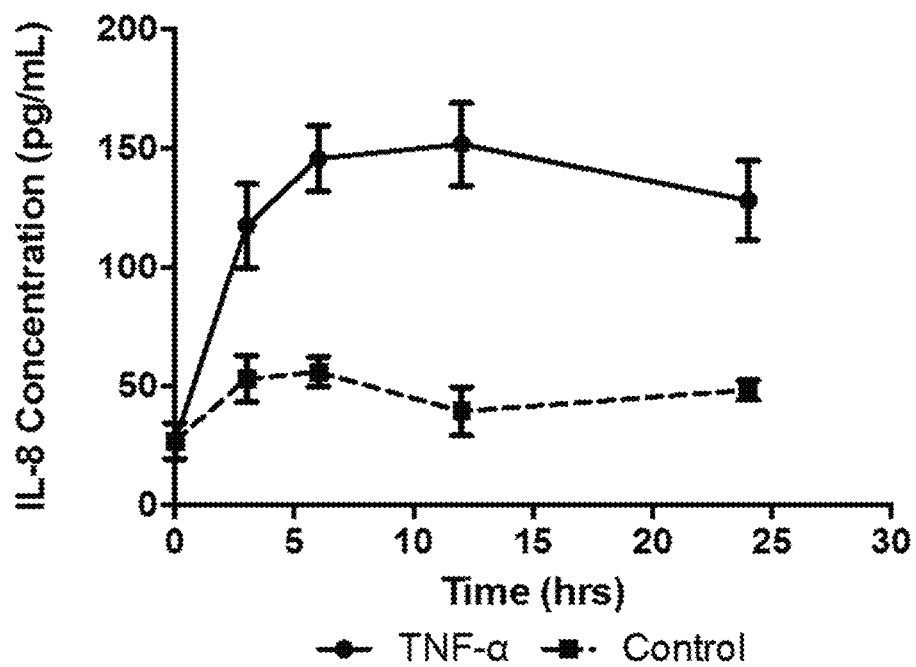
FIG. 9 is a plot showing the levels of IL-8 as a function of time after THP-1 cells ($0.5 \times 10^6$/mL) were stimulated with 10 ng/mL of TNF-α wherein IL-8 secretion in cell culture supernatants was measured at the indicated time points by a single-analyte ELISA. The values presented are mean±SEM (n=3).

Data shown in FIG. 8 and FIG. 9 are the results of experiments carried out to determine the optimal time points of measuring the levels of cytokines after THP-1 cells were treated with LPS or TNF-α. FIG. 8 shows levels of cytokine IL-1β (upper left plot), TNF-α (upper right plot), IL-6 (lower left plot) and IL-8 (lower right plot) secreted from THP-1 cells stimulated with LPS (5 µg/mL) for different durations in comparison to controls. The levels of cytokines IL-1β, TNF-α and IL-8 induced in response to LPS reached peaks by 6-hours post-stimulation. FIG. 9 shows the levels of IL-8 secreted from the THP-1 cells stimulated with TNF-α (10 ng/mL) for different durations. Similar to the results for cytokines IL-1β, TNF-α and IL-8 shown in FIG. 8, the level of IL-8 was plateaued by 6-hour post-stimulation with TNF-α. The only exception observed was the level of IL-6 induced by LPS, which never reached a peak by 24-hour post-stimulation, the last time point used in this experiment. Nevertheless, the 6-hour post-stimulation time point still can be used to measure the relative amounts of secreted IL-6.

Figure 10:
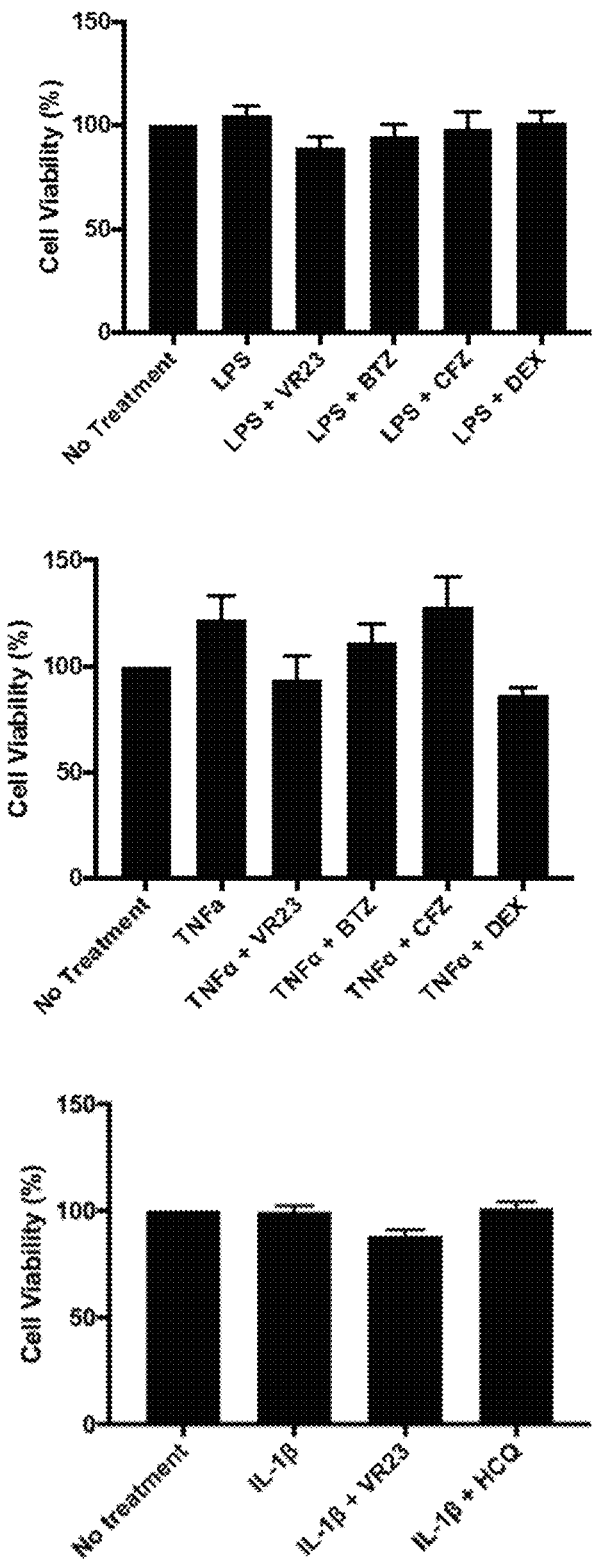
FIG. 10 shows the viability rates of THP-1 (upper and middle plots) and SW-982 (lower plot) cells (5,000 cells/well) after they were treated with LPS (5 μg/mL), TNF-α (10 ng/mL), or IL-1β (1 ng/mL) in the absence or presence of different compounds for 6 hours. Dunnett's test was performed to assess if there are significant differences in cell viability compared to the non-treatment control group. The values presented are mean±SEM (n=3).

Data shown in FIG. 10 were obtained from cell viability assays carried out to ensure that cells are viable under the experimental conditions used to measure the levels of cytokines. In particular, FIG. 10 shows the cell viability rates of THP-1 (upper and middle plots) or SW-982 (lower plot) cells after they were treated with LPS (5 µg/mL), TNF-α (10 ng/mL), or IL-1β (1 ng/mL) in the absence or presence of different compounds for 6 hours. In particular, THP-1 cells (upper and middle plots) and SW-982 cells (lower plot) were treated with cytokine stimulant alone (LPS, TNF-α, or IL-1β) or in combination with VR23, BTZ, CFZ, DEX, or HCQ. The concentrations of agents used for THP-1 cells were as follows: LPS, 5 µg/mL; TNF-α, 10 ng/mL; VR23, 3 µM; BTZ, 6 nM; CFZ, 1 nM; and DEX, 2 µM. The concentrations of agents used for SW-982 cells were as follows: IL-1β, 1 ng/mL; VR23, 5 µM; and HCQ, 30 µM. Upon termination of the experiment at 6-hour post-induction, viable cells were counted using a CCK-8 kit. The CCK-8 assay utilizes the phenomenon that the WST-8 tetrazolium salt gives rise to yellow formazan dye upon reduction by dehydrogenase activities. This yellow formazan dye is directly proportional to the number of living cells (Enzo Life Sciences). The viability of the THP-1 and SW-982 cells did not significantly differ from the untreated cells, while not wishing to be limited by theory, indicating that cells are not dying under these experimental conditions/doses. Accordingly, data obtained under these experimental conditions would not be the result of cell death.

Figure 11:
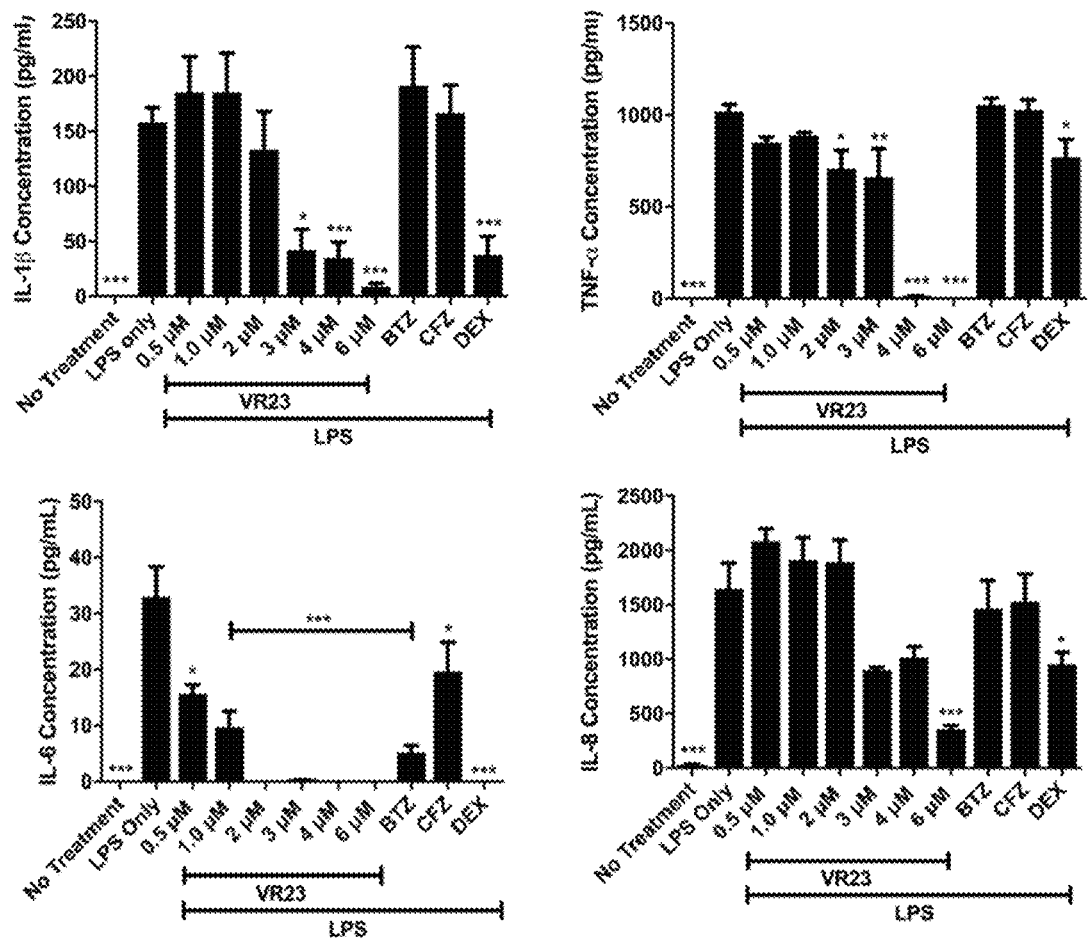
FIG. 11 shows the levels of IL-1β (upper left plot), TNF-α (upper right plot), IL-6 (lower left plot) and IL-8 (lower right plot) in THP-1 cells ($0.5 \times 10^6$/mL) stimulated with 5 µg/mL LPS for 6 hours in the absence (LPS only) or presence of varying concentrations (0.5, 1.0, 2, 3, 4 or 6 µM) of VR23 according to embodiments of the present application. For comparison, BTZ (6 nM), CFZ (1 nM), and DEX (2 µM) were also included. *, , and * are $p<0.05$, $p<0.01$, and $p<0.001$, respectively, which denote a significant difference from the LPS-only group. The mean±SEM (n=3) values were determined by a Dunnett's test.

Data shown in FIG. 11 are the results of experiments carried out to investigate VR23's effect on the levels of inflammatory cytokines. In particular, FIG. 11 shows the levels of IL-1β (upper left plot), TNF-α (upper right plot), IL-6 (lower left plot) and IL-8 (lower right plot) in THP-1 cells stimulated with LPS (5 µg/mL) for 6 hours in the absence (control) or presence of varying concentrations (0.5, 1.0, 2, 3, 4 or 6 µM) of VR23. For comparison, BTZ (6 nM), CFZ (1 nM) and DEX (2 µM) were also included. The levels of cytokine secreted in cell culture supernatants were measured by a single-analyte ELISA. The $IC_{50}$ value of VR23 is 3 µM and the concentrations of BTZ, CFZ and DEX used are their respective $IC_{50}$ values. The results demonstrate that VR23 and DEX show substantial and comparable anti-inflammatory activities, while BTZ and CFZ do not. Treatment with VR23 decreased cytokine secretion in a dose dependent manner. VR23 was especially effective on reducing the level of IL-6 in response to LPS (lower left plot).

Figure 12:
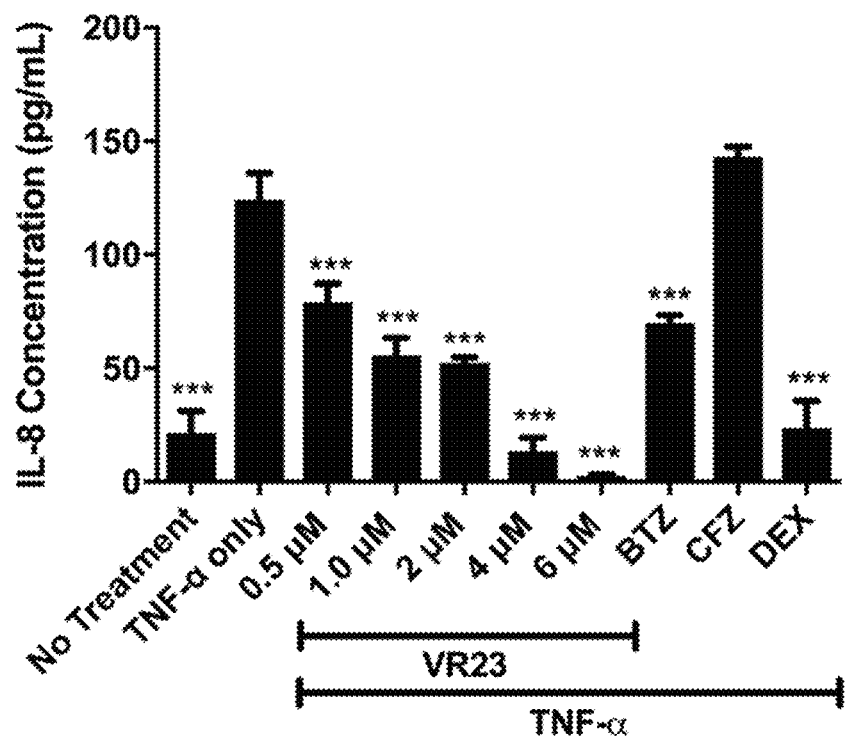
FIG. 12 shows the levels of IL-8 in the supernatant of THP-1 cells ($0.5 \times 10^6$/mL) stimulated with TNF-α (10 ng/mL) for 6 hours in the absence (TNF-α only) or presence of varying concentrations (0.5, 1.0, 2, 4 or 6 µM) of VR23 according to embodiments of the present application. For comparison, BTZ (6 nM), CFZ (1 nM), and DEX (2 µM) were also included. *** is $p<0.001$, which denotes a significant difference from the TNF-α-only group, determined by a Dunnett's test. The values presented are the mean±SEM (n=3).

The data in FIG. 12 show the levels of IL-8 secreted in the THP-1 culture medium in response to TNF-α alone (10 ng/mL) or in combination with varying concentrations (0.5, 1.0, 2, 4 or 6 µM) of VR23. For comparison, BTZ (6 nM), CFZ (1 nM) and DEX (2 µM) were also included. The measurement time was 6-hour post-stimulation. The measurement was carried out with a single-analyte ELISA. VR23 effectively reduces IL-8 secretion at $IC_{50}$ concentration (i.e., between 2 and 4 µM), which is comparable to that of DEX. Furthermore, even at 0.5 µM, VR23 significantly (p<0.001) reduced the level of IL-8. With stimulation with TNF-α, BTZ substantially reduced IL-8, but CFZ was not effective at all.

Figure 13:
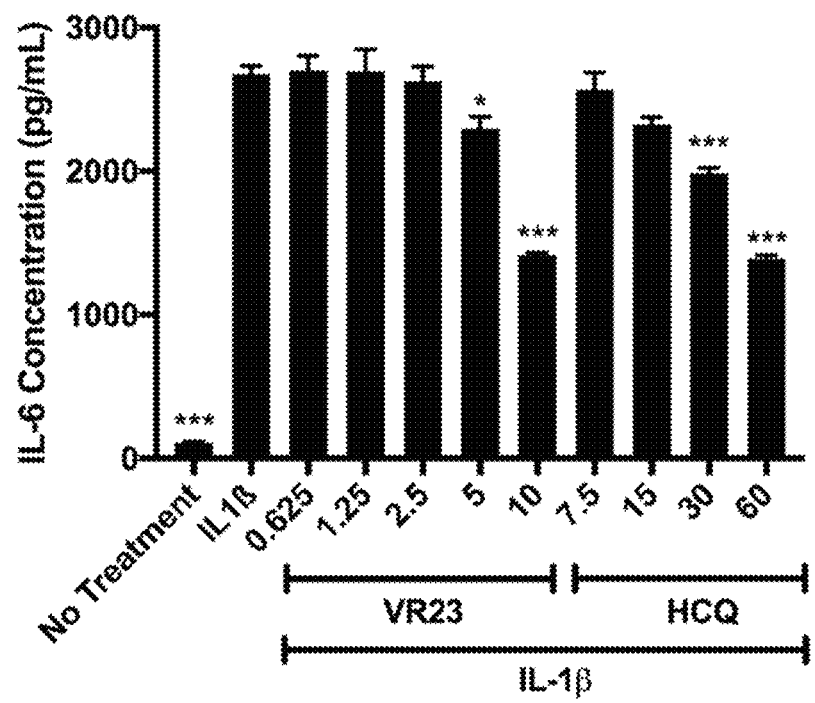
FIG. 13 shows the levels of IL-6 in the supernatant of SW-982 cells ($0.05 \times 10^6$/mL) stimulated with IL-1β (1 ng/mL) for 6 hours in the absence (IL 1β) or presence of varying concentrations of VR23 (0.625, 1.25, 2.5, 5 or 10 µM) according to embodiments of the present application or HCQ (7.5, 15, 30 or 60 µM) for comparison. * and *** are $p<0.05$ and $p<0.001$, respectively, which denote a significant difference from the IL-1β-only group. The mean±SEM (n=2) values were determined by a Dunnett's test.

FIG. 13 shows the levels of IL-6 secreted in the supernatant of SW-982 synovial cells (0.05×10$^6$/mL) stimulated with IL-1β (1 ng/mL) for 6 hours in the absence or presence of varying concentrations of VR23 (0.625, 1.25, 2.5, 5 or 10 μM) or HCQ (7.5, 15, 30 or 60 μM). The measurement was carried out with a single-analyte ELISA. The SW-982 synovial cell line derived from sarcoma is widely used as a model for studying rheumatoid arthritis, as the cell line possesses similar immunological properties as primary synovial cells[28]. While not wishing to be limited by theory, cytokine IL-6 is strongly implicated to the progress of rheumatoid arthritis[29]. VR23 at 10 μM substantially reduced the secretion of IL-6 in the synovial cells stimulated with IL-1β. The reduction rate is comparable to that of the cells treated with the significantly higher concentration of 60 μM HCQ, the agent often used to treat systemic lupus erythematosus and rheumatoid arthritis[30]. Overall, the data indicates that VR23 can be a useful treatment option for certain autoimmune conditions including rheumatoid arthritis and systemic lupus erythematosus.

Figure 14:
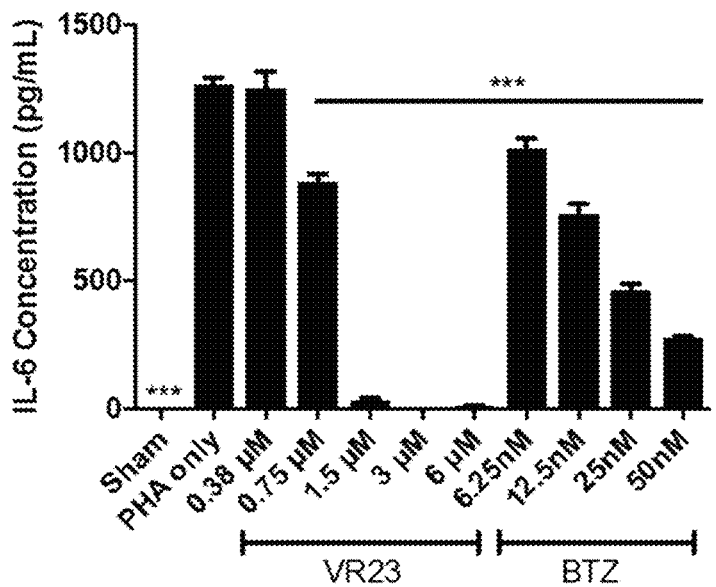
FIG. 14 shows the levels of IL-6 (upper plot) and TNF-α (lower plot) in the supernatant of human peripheral blood mononuclear cells (PBMC; $1 \times 10^6$/mL cells) stimulated with phytohemagglutinin-p (PHA-p; 10 µg/mL) for 6 hours in the absence (PHA only) or presence of varying concentrations of VR23 (0.38, 0.75, 1.5, 3 or 6 µM) according to embodiments of the present application or BTZ (6.25, 12.5, 25 or 50 nM) for comparison. *** is $p<0.001$, which denotes a significant difference from the PHA-only group, determined by a Dunnett's test. The values presented are the mean±SEM (n=2).
Figure 14:
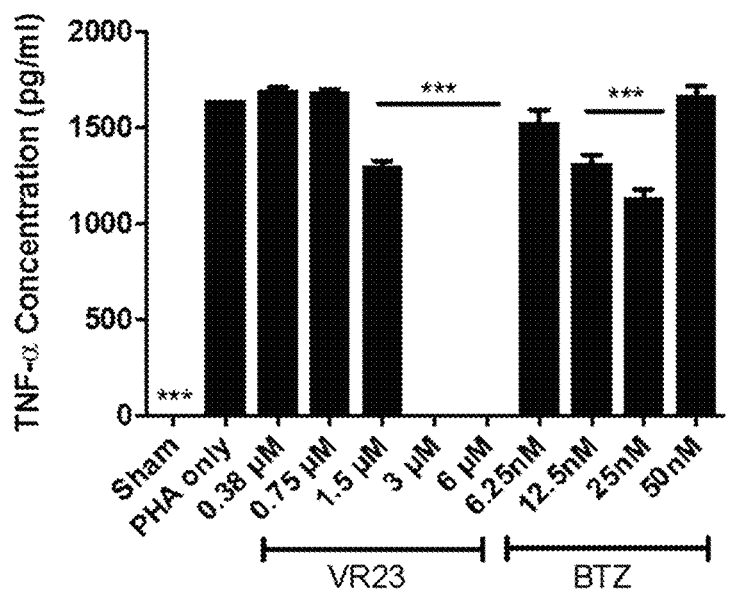

Data in FIG. 14 show the levels of IL-6 (upper plot) and TNF-α (lower plot) in human PBMC (1×10$^6$/mL cells) stimulated with 10 μg/mL phytohemagglutinin-p (PHA-p) (10 μg/mL) for 6 hours, in the absence (control) or presence of varying concentrations of VR23 (0.38, 0.75, 1.5, 3 or 6 μM) or BTZ (6.25, 12.5, 25 or 50 nM). The measurement was carried out with a single-analyte ELISA. The cytokine secretion decreases in a dose dependent manner in both samples. Under the conditions, 1.5 μM (i.e., ½ IC$_{50}$) and 3.0 μM (i.e., IC$_{50}$) of VR23 completely prevented PHA-induced IL-6 and TNF-α, respectively. BTZ also reduced the level of IL-6 at IC$_{50}$ concentration (6 nM). However, BTZ was largely ineffective in reducing the level of TNF-α even at 4× the IC$_{50}$ dose (FIG. 14, lower plot).

VR23 Shows Strong Anti-Inflammatory Activities in Mice.

Since the data from in vitro studies showed that VR23 can substantially reduce or almost completely prevent the secretion of pro-inflammatory cytokines in THP-1, SW-982, and PBMC cells, its anti-inflammatory effects in a mouse model were examined. Toward this goal, a useful LPS dose to induce TNF-α in the mouse bronchoalveolar fluid was first obtained. Data shown in FIG. 1 indicated that 0.4 mg LPS per kg body weight would be a useful dose when the subjected animals' lungs were analyzed at 24-hour post-LPS; for example, a useful dose of LPS would be one that can instigate a sufficient immune response without causing any notable damage. Acute lung injury was characterized by an increased permeability of the capillary barrier, which is accompanied by an increase in lung edema and an influx of neutrophils into the bronchoalveolar space[31]. The influx of neutrophils caused by ALI induces the release of pro-inflammatory cytokines such as IL-1β, TNF-α, and IL-8[31]. To illustrate the anti-inflammatory property of VR23, the level of TNF-α in the BALF was measured at 24-hour post-treatment. FIG. 2 shows the effects of VR23 on the total cell counts per mL of the bronchoalveolar fluid of mice with acute lung injury induced with LPS in comparison to treatment with DEX as well as various controls. The total number of cells recruited into the bronchoalveolar space was completely prevented by VR23 at 30 mg/kg which was more effective than DEX. FIG. 3 shows the effect of VR23 on the levels of the TNF-α inflammatory cytokine in the bronchoalveolar lavage fluid (BALF) of BALB/c mice with ALI caused by LPS. The levels of TNF-α were determined at 24-hour post-LPS stimulation (0.4 mg/kg), in the absence (controls) or presence of DEX (4 mg/kg) or VR23 (30 mg/kg). The data in FIG. 3 show that VR23 effectively reduces the level of TNF-α.

VR23 is a Strong Inhibitor of Myeloperoxidase (MPO), a Marker Distinctly Correlated with Inflammation.

Neutrophils that influx into the bronchoalveolar space due to ALI caused by inflammatory stimuli such as LPS degranulate and release the pro-inflammatory enzyme MPO[32]. Therefore, the levels of MPO can be a useful inflammation marker[38]. FIG. 4 shows the effects of VR23 on the myeloperoxidase in the lung tissues of mice with ALI caused by LPS. The data in FIG. 4 show that VR23 is a strong inhibitor of MPO, via preventing the influx of neutrophils into inflammation sites.

Histopathological Data Show that VR23 (30 mg/kg) Inhibits the Influx of Immune Cells into the Lung Alveolar Space.

LPS-induced ALI can lead to the inflammation of lung tissues due to the influx of immune cells into the alveolar space. The lung tissue sections stained with hematoxylin and eosin (H & E) show that alveolar inflammation caused by LPS (FIG. 5, upper right image) is largely prevented when animals were treated with 30 mg/kg VR23 (FIG. 5, lower left image) or (4 mg/kg) of DEX (FIG. 5, lower right image).

VR23 Effectively Reduces or Largely Prevents the Secretion of IL-6 Pro-Inflammatory Cytokine in Human Synovial Cells.

Figure 15:
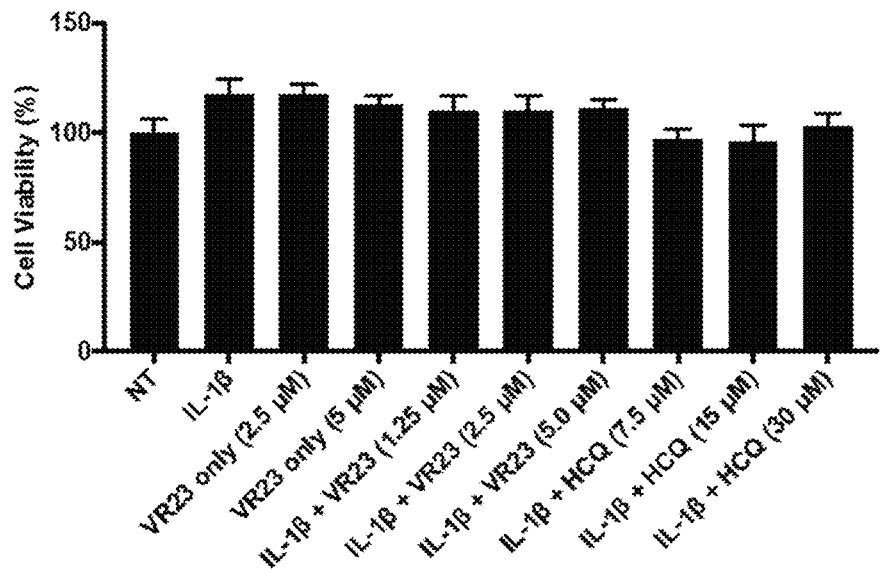
FIG. 15 shows the results of viability tests carried out with human fibroblast-like synoviocytes from rheumatoid arthritis patients (HFLS-RA) (upper plot) and human fibroblast-like synoviocytes from healthy donors (HFLS-N) (lower plot), measured at 6-hour post-stimulation with VR-23 alone (upper plot: 2.5 or 5 µM; lower plot: 5 µM) according to embodiments of the present application, or IL-1β alone (10 ng/mL) or in the presence of varying concentrations of VR23 (upper plot: 1.25, 2.5 or 5.0 µM; lower plot 2.5, 5 or 10 µM) according to embodiments of the present application and HCQ (both plots: 7.5, 15 or 30 µM) for comparison. * is $p<0.05$ and denotes a significant difference from the non-treatment group, determined by a Dunnett's test. The values presented are the mean±SEM (n=3).
Figure 15:
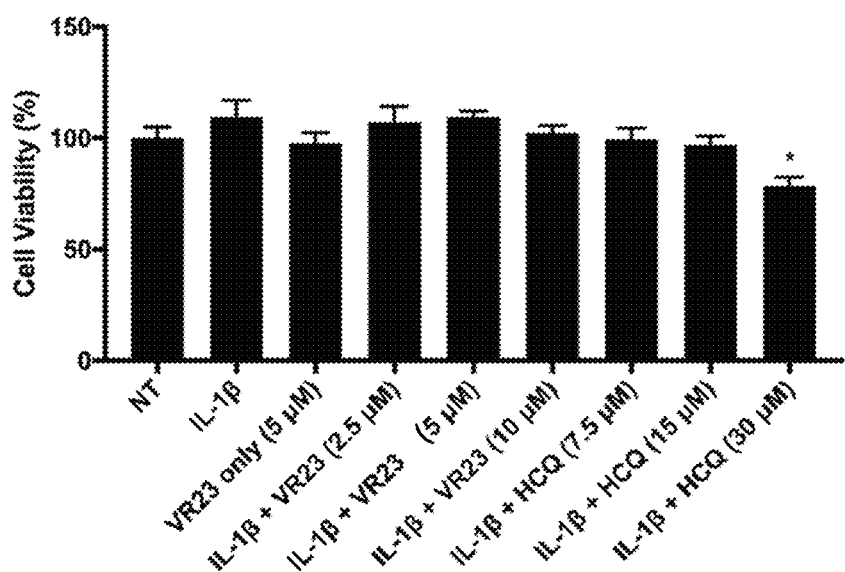
Figure 16:
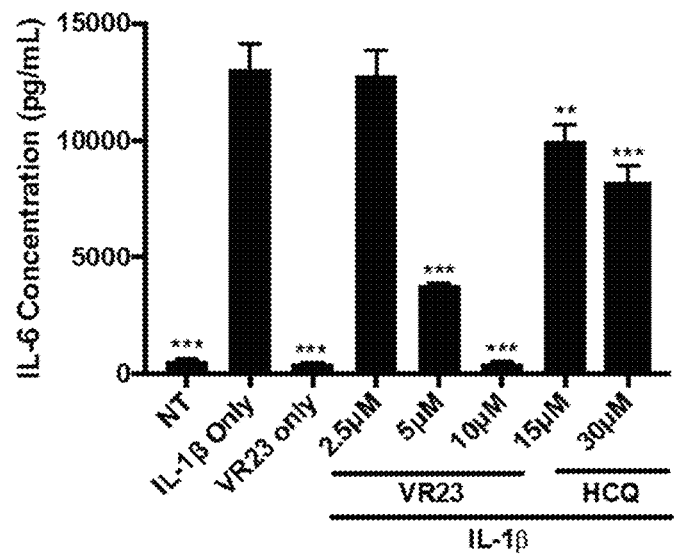
FIG. 16 shows the levels of IL-6 in HFLS-RA (upper plot) and HFLS-N (lower plot) cells at 6-hour post-stimulation with IL-1β (10 ng/mL) in the absence (control; IL-1β only) or presence of varying concentrations of VR23 (2.5, 5 or 10 µM) according to embodiments of the present application or HCQ (15 or 30 µM) for comparison, as well as in the presence of VR23 alone (VR23 only; 5 µM) according to embodiments of the present application.  and * are $p<0.01$ and $p<0.001$, denote a significant difference from the IL-1β-only group. The mean±SEM (n=3) values were determined by a Dunnett's test.
Figure 16:
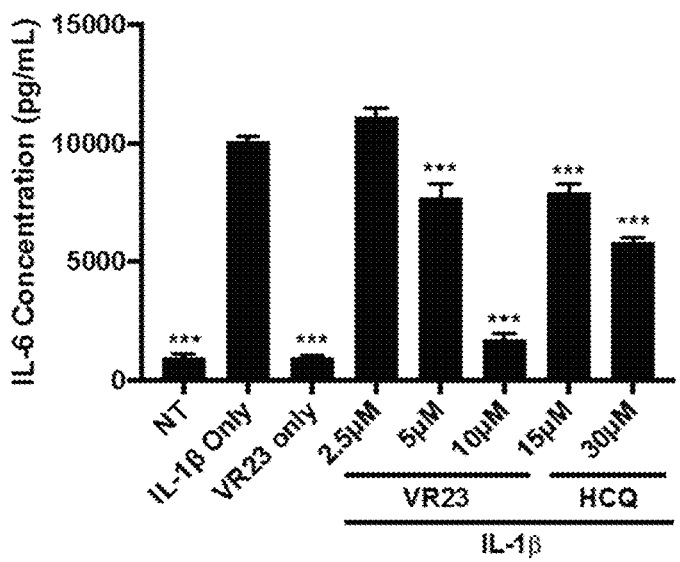
Figure 17:
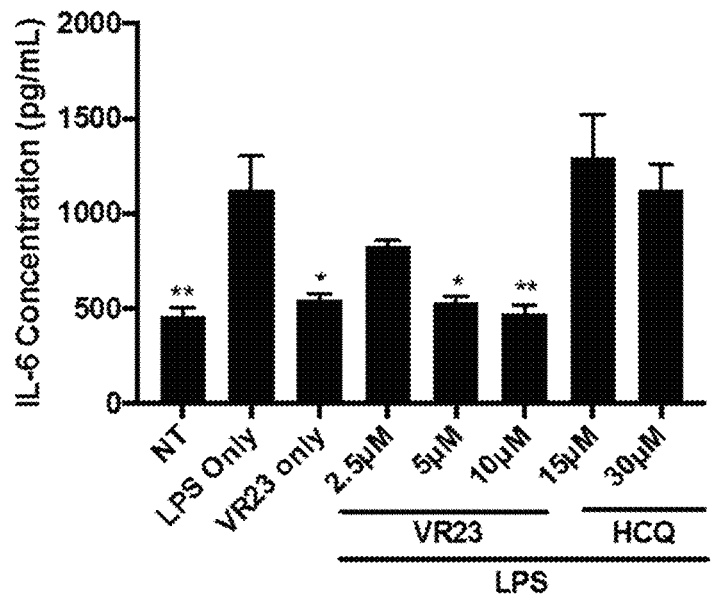
FIG. 17 shows the levels of IL-6 in HFLS-RA (upper plot) and HFLS-N (lower plot) cells at 6-hour post-stimulation with LPS (100 ng/mL) in the absence (control; LPS only) or presence of varying concentrations of VR23 (2.5, 5 or 10 µM) according to embodiments of the present application or HCQ (15 or 30 µM) for comparison, as well as in the presence of VR23 alone (VR23 only; 5 µM) according to embodiments of the present application. * and ** are $p<0.05$ and $p<0.01$, respectively, and denote a significant difference from the LPS-only group determined by a Dunnett's test. The values presented are the mean±SEM (n=2).
Figure 17:
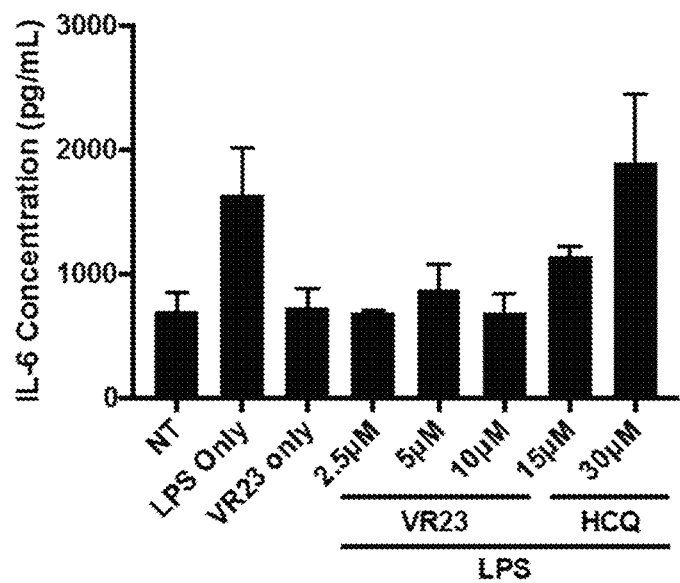

As shown above, the data from in vitro and animal models showed that VR23 has a strong anti-inflammation activity. This finding was extended to human cells relevant to autoimmune diseases. Human fibroblast-like synoviocytes (HFLS) are present in the synovial fluid of joint capsules and produce harmful molecules that contribute to joint destruction and the exacerbation of the disease in rheumatoid arthritis patients. First, conditions that are potentially effective but do not kill cells at 6-hour post-stimulation were determined. FIG. 15 shows the results of viability tests with HFLS-RA (upper plot) and HFLS-N (lower plot) cells (5,000 cells/well) measured at 6-hour post-stimulation in the absence (control) or presence of varying concentrations of VR23 or HCQ. As shown in FIG. 15, none of the conditions examined significantly affected the viability of fibroblast-like synovial cells from either rheumatoid arthritis patients (HFLS-RA) (upper plot) or from non-rheumatic patient control (HFLS-N) (lower plot), except HFLS-N treated with IL-1β plus 30 μM of HCQ (lower plot). The cells were then stimulated with IL-1β (FIG. 16) or LPS (FIG. 17), in the absence (control; IL-1β only) or presence of VR23 or HCQ. HCQ was included for comparison because it is often used to treat rheumatoid arthritis. FIG. 16 shows the levels of IL-6 in HFLS-RA (upper plot) and HFLS-N (lower plot) cells at 6-hour post-stimulation with IL-1β in the absence (controls) or presence of varying concentrations of either VR23 or HCQ. For "VR23 only" samples, 5 μM VR23 was used. Fifty thousand HFLS cells per mL were used for the experiment. Cytokine levels in cell culture supernatants were determined by a single-analyte ELISA. Note that the cytokine secretion decreases in a dose dependent manner for samples treated with either VR23 or HCQ. While not wishing to be limited by theory, it is interesting and potentially important that VR23 at 5 μM reduces the level of IL-6 secretion more effectively on HFLS-RA than HFLS-N (FIG. 16). FIG. 17 shows the levels of IL-6 in the supernatant of HFLS-RA (A) and HFLS—N(B) cells treated for 6 hours with LPS alone (100 ng/mL) or in the presence of varying concentrations of VR23 or HCQ. Fifty thousand HFLS cells per mL were used for the experiment. The cytokine secretion was measured in cell culture supernatants by a single-analyte ELISA. The secretion of IL-6 in HFLS-RA cells decreased substantially in the presence of 5 or 10 µM of VR23. The rate of the decrease is much lower in HFLS-N cells, while not wishing to be limited by theory, raising the possibility that there is an opportunity of a useful therapeutic window by VR23 with minimum effects on normal synovial cells. VR23 was much more effective overall than HCQ. For example, 5 µM VR23 was significantly more effective than the much higher concentration 30 µM of structurally similar HCQ on the synovial cells from rheumatoid arthritis patients (FIG. 16 and FIG. 17).

VR23 Prevents Synovial Cell Migration.

Figure 18:
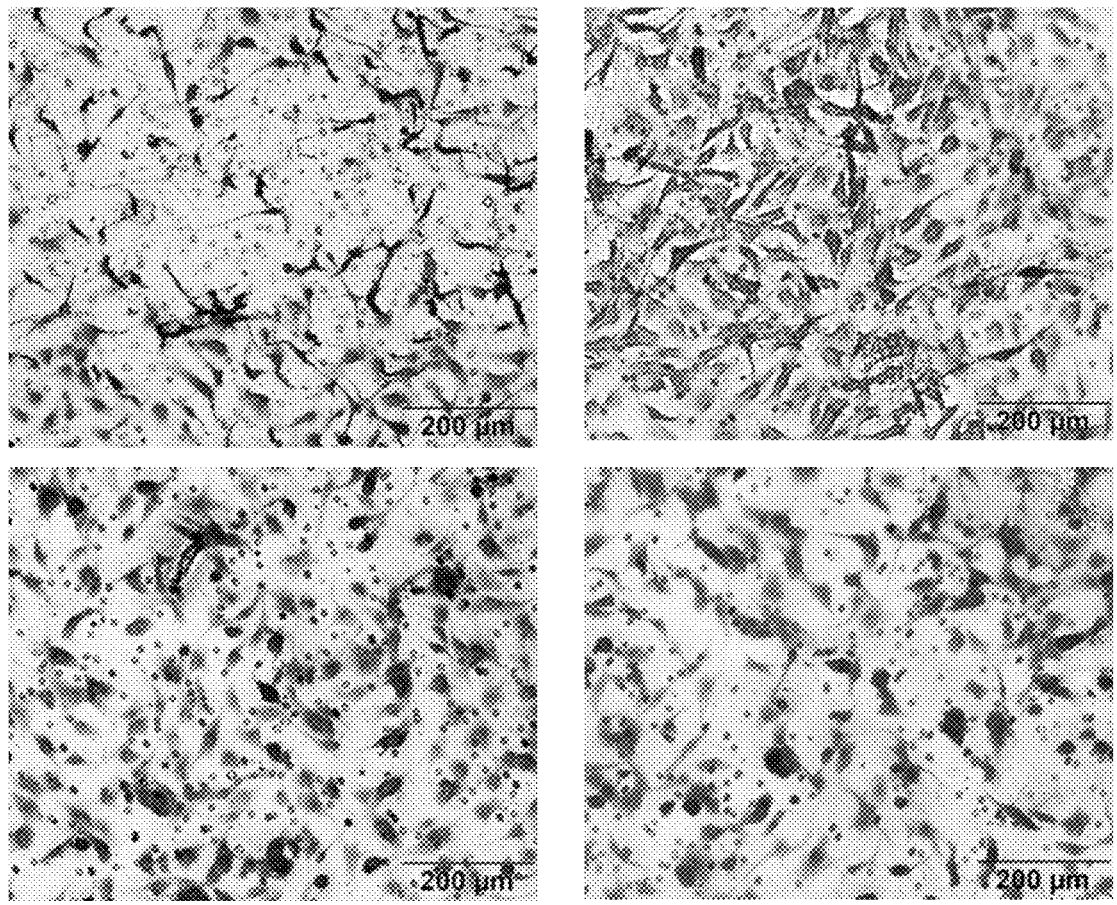
FIG. 18 shows exemplary micrographs showing that treatment with VR23 according to embodiments of the present application prevents HFLS-RA cell migration wherein the cell migration of the HFLS-RA cells was measured using a Corning matrigel-coated invasion-chamber (8-µM pore) (Fisher Scientific) that was treated for 24 hours with 10% (vol/vol) fetal bovine serum (FBS) as chemo-attractant, in the absence or presence of VR23 (5 µM or 10 µM): no FBS (upper left image), 10% FBS in the lower chamber (upper right image), 10% FBS+5 µM VR23 in the lower chamber (lower left image), and 10% FBS+10 µM VR23 in the lower chamber (lower right image). Scale bars show 200 µm.
Figure 19:
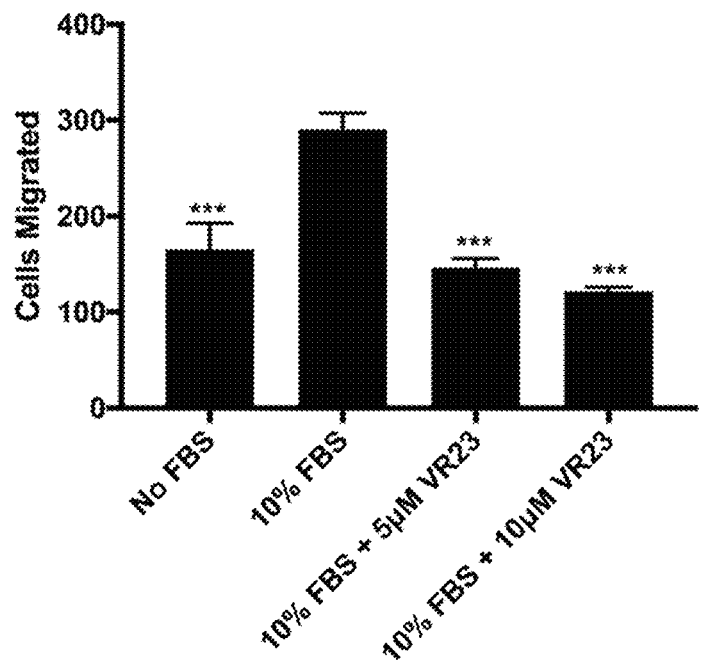
FIG. 19 shows a plot of the quantitative data for the migrated cells shown in FIG. 18 and that treatment with 5 µM or 10 µM of VR23 according to embodiments of the present application completely prevents cell migration promoted by the stimulation of HFLS-RA with 10% FBS. *** is $p<0.001$ and denotes a significant difference from the 10% FBS group determined by a Dunnett's test. The values presented are the mean±SEM (n=2).

Synovial cells contribute to joint destruction by invading the joint cartilage, where they secrete inflammatory molecules harmful to the organ. Therefore, the inhibition of synovial cell migration is an effective way of delaying or preventing joint destruction. Data shown in FIG. 18 and FIG. 19 demonstrate that 5 µM or 10 µM VR23 significantly or completely prevent synovial cell migration. FIG. 19 shows that VR23 (5 µM or 10 µM) completely prevents cell migration promoted by 10% FBS in HFLS-RA. Data in FIG. 19 are quantitation of the migrated cells shown in FIG. 18.

VR23 Possesses Anti-Malarial Activity.

Figure 20:
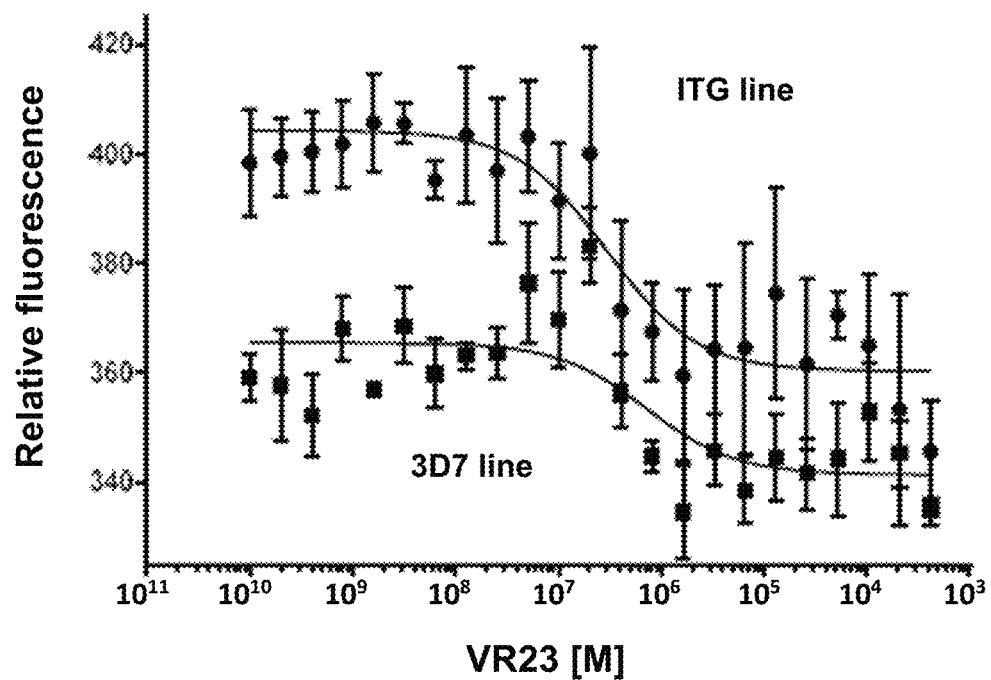
FIG. 20 is a plot of the relative fluorescence as a function of VR23 concentration (M) according to embodiments of the present application for *P. falciparum* strains ItG (upper line) and 3D7 (lower line). The $IC_{50}$ values of VR23 against these strains are 117 nM (S.E.M.) and 416 nM (S.E.M.), respectively.

VR23 is a derivative of CQ; a well-known anti-malarial drug. FIG. 20 shows that VR23 shows anti-malarial activity. ItG and 3D3 *P. falciparum* strains are CQ-resistant and CQ-sensitive strains, respectively. $IC_{50}$ values were calculated by S.E.M (Table 2). The data shown in FIG. 20 and Table 2 demonstrate that VR23 does possess anti-malarial activity. Surprisingly, VR23 is more effective on the CQ-resistant ItG strain than the CQ-sensitive 3D7 strain ($IC_{50}$ values of 117 nM vs 416 nM).

TABLE 2

| $IC_{50}$ values for VR23 | | |
| --- | --- | --- |
| *P. falciparum* strains | ItG | 3D7 |
| VR23 ($IC_{50}$, nM) | 117 | 416 |

III. Summary and Discussion

VR23 is a proteasome inhibitor targeting (32 of the 20S proteasome catalytic subunit[2]. Previous studies showed that VR23 is not only non-toxic to normal mouse organs, but also reduces toxic side effects caused by paclitaxel when used in combination[2].

IL-6 is a pleiotropic cytokine that is produced at the site of inflammation[33]. Its dysregulation may lead to the development and exacerbation of chronic inflammatory diseases such as rheumatoid arthritis, systemic lupus erythematosus and Crohn's disease[29,33]. These autoimmune conditions are associated with a high level of circulating IL-6, correlating it to high disease activities[33]. In rheumatoid arthritis, many inflammatory cells infiltrate the synovium, leading to synovial lining hyperplasia[34]. Among inflammatory cells recruited, the fibroblast-like synoviocytes (FLS) have emerged as strong pro-inflammatory cells that promote the progression of the disease. Human FLS cells are resident mesenchymal cells of synovial joints that produce synovial fluid to line the joint. In rheumatoid arthritis, HFLS can cause destruction of the joint and contribute to the prolongation of the disease by recruiting and sustaining the immune response through the secretion of pro-inflammatory mediators[34]. Thus, HFLS was selected as a model system in the present study. Due to the over-production of IL-6 in inflammatory diseases, it has been the target for novel treatments for chronic inflammatory diseases[33]. Indeed, treatment efficacy of rheumatoid arthritis was correlated with a drug's ability to lowering the level of IL-6 secretion[29].

In addition to cell-based studies, the anti-inflammatory effects of VR23 were examined using a mouse model with an ALI. Acute lung injury is a severe respiratory disorder that is characterized by lung inflammation and increased vascular permeability[35]. The disorder is most commonly caused by sepsis or pneumonia resulting from bacterial infection, especially LPS-producing gram negative bacteria[35]. Acute lung injury caused by LPS may lead to an increase in microvascular permeability, causing high levels of proteins and macromolecules in the fluid of the bronchoalveolar space[31]. This, in turn, may result in lung edema and an influx of neutrophils into the bronchoalveolar space, leading to the secretion of inflammatory cytokines and chemokines including TNF-α, IL-1=β8, and IL-6[35,36]. Therefore, an ALI is a useful model to study in vivo potential new drugs for the treatment of anti-inflammation.

Data from in vitro THP-1 cell-based studies presented in this example demonstrate that VR23 effectively reduces the secretion of pro-inflammatory cytokines such as IL-1β, TNF-α, IL-6 and IL-8 (FIG. 11 and FIG. 12). The VR23-mediated reduction of pro-inflammatory cytokines was comparable to that by DEX. However, VR23 has advantages over DEX in that, for example, VR23 was found to have been non-toxic and it is non-steroidal.

Other proteasome inhibitors such as BTZ and CFZ do not effectively reduce the secretion of pro-inflammatory cytokines (FIG. 11 and FIG. 12). Proteasome inhibitors including BTZ were originally thought to down-regulate inflammation by interfering with the nuclear factor-KB pathway. However, recent studies suggest that BTZ may actually induce inflammation via the nuclear factor-KB pathway[37]. While many anticancer agents are pro-inflammatory, VR23 was found to an anti-inflammatory agent, which may, for example, make it uniquely advantageous for the treatment of cancer patients with chronic inflammation.

Data from the study with the SW-982 synovial cells demonstrate that the down-regulation of IL-6 by VR23 is comparable to that by HCQ, surprisingly, even when the VR23 is used at a substantially lower dose (FIG. 13). HCQ is often used at clinics to treat rheumatoid arthritis and systemic lupus, indicating that VR23 may have the potential of treating these diseases with advantageous results.

Consistent with data from THP-1 cell-based studies (FIG. 11 and FIG. 12), the results from PBMC-based studies show that VR23 dramatically reduced the secretion of IL-6 and TNF-α pro-inflammatory cytokines (FIG. 14). VR23 also effectively reduced the levels of IL-6 stimulated with IL-18 (FIG. 16, upper plot) or LPS (FIG. 17, upper plot) in fibroblast like synoviocytes from rheumatoid arthritis patients. Thus, the inhibitory effect of VR23 on the secretion of inflammatory cytokines may, for example be clinically relevant.

The fact that VR23 effectively reduces the levels of inflammatory cytokines, especially that of IL-6, indicates that VR23 may be useful to treat many different chronic inflammatory and autoimmune disorders, including rheumatoid arthritis, systemic lupus erythematosus, and Crohn's disease[33].

Data from mice with LPS-mediated ALI showed that VR23 effectively reduces the level of TNF-α and total invaded cell numbers in the bronchoalveolar fluid. The efficacy is comparable to that of DEX (FIG. 2 and FIG. 3), one of the most effective agents used to treat inflammatory and allergic disease[38]. However, VR23 may have advantages over DEX for a number of reasons: (i) VR23 is not a steroid; therefore, it does not have side effects caused by steroids; (ii) VR23 showed no toxicity to normal mouse organs[2]; and (iii) VR23 reduces toxic side effects caused by a partner drug when used in combination[2].

Data from the mouse ALI model also showed that VR23 effectively reduced the level of MPO in the bronchoalveolar space (FIG. 4). An MPO assay is used to determine the influx of neutrophils into the bronchoalveolar space. The effect of MPO reduction by VR23 was comparable to that of DEX. Since an elevated level of MPO is a risk factor for cardiovascular related mortality[39], VR23 may also have potential for the treatment of cardiovascular conditions.

The anti-inflammatory effect of VR23 was further observed by histopathological analysis of alveolar tissues (FIG. 5).

Since VR23 reduces the levels of TNF-α and IL-6, it may, for example, be useful for treatment of aging-related diseases including dementia, stroke, frailty and clearing of microbial infections, for example *S. pneumonia*.

VR23, a CQ derivative, was effective against *P. falciparum* (FIG. 20). In particular, at an $IC_{50}$ value of 117 nM, VR23 was an especially effective agent against the CQ-resistant ItG strain. Thus, VR23 shows useful potential as an effective anti-malarial drug, for example for those refractory to CQ. *P. falciparum* is known to involve in the development of blood cancers[19,20]. Since VR23 can control both cancer[2] and *P. falciparum*, it may, for example, be especially advantageous to treat cancer patients with *P. falciparum* infection.

In conclusion, VR23 may be useful for the control of many different diseases including inflammatory disorders, autoimmune diseases, and malarial infections. As described above, VR23 did not show any notable ill-effects to normal organs in the mouse[2]. Furthermore, VR23 reduced toxic side effects caused by a partner drug when used in combination[2]. Thus, VR23 may be useful for the treatment of these diseases, alone or in combination with other agents.

While the present application has been described with reference to what are presently considered to be the preferred examples, it is to be understood that the application is not limited to the disclosed examples. To the contrary, the present application is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

FULL CITATIONS FOR DOCUMENTS REFERRED TO IN THE SPECIFICATION

[1] PCT Application Publication No. 2014/134705 A1.
[2] Pundir, S., et al., *VR23: A Quinoline-Sulfonyl Hybrid Proteasome Inhibitor That Selectively Kills Cancer via Cyclin E-Mediated Centrosome Amplification*. Cancer Res, 2015. 75(19): p. 4164-75.
[3] Statistics Canada, Table 13-10-0394-01: *Leading causes of death, total population, by age group*. 2016.
[4] Shah, A., D. Fitzgerald, and F. Murray, *Non-steroidal anti-inflammatory drugs (NSAIDs) and gastro-intestinal toxicity: Current issues*. Irish Journal of Medical Science, 1999. 168(4): p. 242-245.
[5] Bhala, N., et al., *Vascular and upper gastrointestinal effects of non-steroidal anti-inflammatory drugs: meta-analyses of individual participant data from randomised trials*. Lancet, 2013. 382: p. 769-779.
[6] Barnes, P. J., *Anti-inflammatory actions of glucocorticoids: molecular mechanisms*. Clinical Science, 1998. 94(6): p. 557-572.
[7] Moghadam-Kia, S. and V. P. Werth, *Prevention and treatment of systemic glucocorticoid side effects*. International Journal of Dermatology, 2010. 49(3): p. 239-248.
[8] Aulakh, R. and S. Singh, *Strategies for minimizing corticosteroid toxicity: a review*. The Indian Journal of Pediatrics, 2008. 75(10): p. 1067-1073.
[9] The Autoimmune Diseases Coordinating Committee, *Progress in Autoimmune Disease Research*, in *Report to Congress*. 2005, National Institute of Allergy and Infectious Diseases, National Institutes of Health: Bethesda, Md.
[10] Verbrugge, S. E., et al., *Proteasome inhibitors as experimental therapeutics of autoimmune diseases*. Arthritis Research & Therapy, 2015. 17(1): p. 17.
[11] Forlenza, O. V., et al., *Increased serum IL-1beta level in Alzheimer's disease and mild cognitive impairment*. Dement Geriatr Cogn Disord, 2009. 28(6): p. 507-12.
[12] Whiteley, W., et al., *Inflammatory markers and poor outcome after stroke: a prospective cohort study and systematic review of interleukin-6*. PLoS Med, 2009. 6(9): e1000145.
[13] Cesari, M., et al., *Inflammatory markers and onset of cardiovascular events: results from the Health ABC study*. Circulation, 2003. 108(19): p. 2317-22.
[14] Li, H., B. Manwani, and S. X. Leng, *Frailty, inflammation, and immunity*. Aging Dis, 2011. 2(6): p. 466-73.
[15] Giovannini, S., et al., *Interleukin-6, C-reactive protein, and tumor necrosis factor-alpha as predictors of mortality in frail, community-living elderly individuals*. J Am Geriatr Soc, 2011. 59(9): p. 1679-85.
[16] Puchta, A., et al., *TNF Drives Monocyte Dysfunction with Age and Results in Impaired Anti-pneumococcal Immunity*. PLoS Pathog, 2016. 12(1): e1005368.
[17] Paats, M. S., et al., *Local and systemic cytokine profiles in nonsevere and severe community-acquired pneumonia*. Eur Respir J, 2013. 41(6): p. 1378-85.
[18] Yende, S., et al., *Inflammatory markers at hospital discharge predict subsequent mortality after pneumonia and sepsis*. Am J Respir Crit Care Med, 2008. 177(11): p. 1242-7.
[19] De Flora, S. and S. La Maestra, *Epidemiology of cancers of infectious origin and prevention strategies*. J Prev Med Hyg, 2015. 56(1): p. E15-20.
[20] van Tong, H., et al., *Parasite Infection, Carcinogenesis and Human Malignancy*. EBioMedicine, 2017. 15: p. 12-23.
[21] Vichai, V. and K. Kirtikara, *Sulforhodamine B colorimetric assay for cytotoxicity screening*. Nature Protocols, 2006. 1(3): p. 1112.
[22] Hu, C., et al., *The efficacy and selectivity of tumor cell killing by Akt inhibitors are substantially increased by chloroquine*. Bioorganic & Medicinal Chemistry, 2008. 16(17): p. 7888-7893.

[23] Skehan, P., et al., *New colorimetric cytotoxicity assay for anticancer-drug screening.* J Natl Cancer Inst, 1990. 82(13): p. 1107-12.

[24] Justus, C. R., et al., *In vitro cell migration and invasion assays.* Journal of Visualized Experiments: JoVE, 2014. 88: 51046.

[25] Crandall, I. E., et al., *Antimalarial activities of 6-iodouridine and its prodrugs and potential for combination therapy.* J Med Chem, 2013. 56(6): p. 2348-58.

[26] Wei, D. and Z. Huang, *Anti-inflammatory effects of triptolide in LPS-induced acute lung injury in mice.* Inflammation, 2014. 37(4): p. 1307-1316.

[27] (a) Jeong, J.-Y. and D.-M. Jue, *Chloroquine inhibits processing of tumor necrosis factor in lipopolysaccharide-stimulated RAW 264.7 macrophages.* The Journal of Immunology, 1997. 158(10): p. 4901-4907; (b) Karres, I., et al., *Chloroquine inhibits proinflammatory cytokine release into human whole blood.* American Journal of Physiology-Regulatory, Integrative and Comparative Physiology, 1998. 274(4): p. R1058-R1064; (c) Picot, S., et al., *Chloroquine inhibits tumor necrosis factor production by human macrophages in vitro.* J Infect Dis, 1991. 164(4): p. 830; (d) Zhu, X., et al., *Chloroquine inhibits macrophage tumour necrosis factor-alpha mRNA transcription.* Immunology, 1993. 80(1): p. 122.

[28] Chang, J.-H., et al., *Validity of SW982 synovial cell line for studying the drugs against rheumatoid arthritis in fluvastatin-induced apoptosis signaling model.* The Indian Journal of Medical Research, 2014. 139(1): p. 117.

[29] Yoshida, Y. and T. Tanaka, *Interleukin 6 and rheumatoid arthritis.* BioMed Research International, 2014. 698313.

[30] (a) Clark, P., et al., *Hydroxychloroquine Compared with Placebo in Rheumatoid Arthritis: A Randomized, Controlled Trial.* Annals of Internal Medicine, 1993. 119(11): p. 1067-1071; (b) Molad, Y., et al., *Protective effect of hydroxychloroquine in systemic lupus erythematosus. Prospective long-term study of an Israeli cohort.* Lupus, 2002. 11(6): p. 356-361; (c) Ben-Zvi, I., et al., *Hydroxychloroquine: from malaria to autoimmunity.* Clinical Reviews in Allergy & Immunology, 2012. 42(2): p. 145-153.

[31] Grommes, J. and O. Soehnlein, *Contribution of neutrophils to acute lung injury.* Molecular Medicine, 2011. 17(3-4): p. 293.

[32] Pulli, B., et al., *Measuring myeloperoxidase activity in biological samples.* PloS One, 2013. 8(7): p. e67976.

[33] Gabay, C., *Interleukin-6 and chronic inflammation.* Arthritis Research & Therapy, 2006. 8(2): p. S3.

[34] Noss, E. H. and M. B. Brenner, *The role and therapeutic implications of fibroblast-like synoviocytes in inflammation and cartilage erosion in rheumatoid arthritis.* Immunological reviews, 2008. 223(1): p. 252-270.

[35] Ni, Y.-F., et al., *Histone deacetylase inhibitor, butyrate, attenuates lipopolysaccharide-induced acute lung injury in mice.* Respiratory Research, 2010. 11(1): p. 33.

[36] Wang, D., et al., *Peptidoglycans promotes human leukemic THP-1 cell apoptosis and differentiation.* Asian Pacific Journal of Cancer Prevention, 2012. 13(12): p. 6409-6413.

[37] (a) Kraus, J., et al., *The novel β2-selective proteasome inhibitor LU-102 decreases phosphorylation of I kappa B and induces highly synergistic cytotoxicity in combination with ibrutinib in multiple myeloma cells.* Cancer Chemotherapy and Pharmacology, 2015. 76(2): p. 383-396; (b) Jia, L., et al., *Blocking autophagy prevents bortezomib-induced NF-κB activation by reducing I-κBa degradation in lymphoma cells.* PloS One, 2012. 7(2): p. e32584.

[38] Ali, A., et al., *Novel N-arylpyrazolo [3, 2-c]-based ligands for the glucocorticoid receptor: receptor binding and in vivo activity.* Journal of Medicinal Chemistry, 2004. 47(10): p. 2441-2452.

[39] Heslop, C. L., J. J. Frohlich, and J. S. Hill, *Myeloperoxidase and C-reactive protein have combined utility for long-term prediction of cardiovascular mortality after coronary angiography.* J Am Coll Cardiol, 2010. 55(11): p. 1102-9.

The invention claimed is:

1. A method of treating a disease, disorder or condition treatable by reducing or inhibiting the secretion of a pro-inflammatory cytokine and/or reducing myeloperoxidase levels, the method comprising administering a therapeutically effective amount of 7-chloro-4-(4-(2,4-dinitrophenylsulfonyl)piperazin-1-yl)quinoline or a pharmaceutically acceptable salt, solvate or prodrug thereof to a subject in need thereof, wherein the disease, disorder or condition is rheumatoid arthritis.

2. The method of claim 1, wherein 7-chloro-4-(4-(2,4-dinitrophenylsulfonyl)piperazin-1-yl)quinoline is administered to the subject.

3. The method of claim 1, wherein the pro-inflammatory cytokine is selected from IL-1β, TNF-α, IL-6, IL-8 and combinations thereof.

4. The method of claim 1, wherein the subject is a human.

* * * * *